US007186278B2

(12) United States Patent
Plos et al.

(10) Patent No.: US 7,186,278 B2
(45) Date of Patent: Mar. 6, 2007

(54) COMPOSITION FOR DYEING HUMAN KERATIN MATERIALS, COMPRISING AT LEAST ONE FLUORESCENT DYE AND AT LEAST ONE COMPOUND COMPRISING AN ACID FUNCTIONAL GROUP AND PROCESSES THEREFOR

(75) Inventors: Grégory Plos, Paris (FR); Luc Gourlaouen, Asnieres (FR)

(73) Assignee: L'Oreal S.A., Paris (FR)

( * ) Notice: Subject to any disclaimer, the term of this patent is extended or adjusted under 35 U.S.C. 154(b) by 346 days.

(21) Appl. No.: 10/814,430

(22) Filed: Apr. 1, 2004

(65) Prior Publication Data

US 2004/0256598 A1 Dec. 23, 2004

Related U.S. Application Data

(60) Provisional application No. 60/468,078, filed on May 6, 2003.

(30) Foreign Application Priority Data

Apr. 1, 2003 (FR) ................................ 03 04029

(51) Int. Cl.
*A61K 7/13* (2006.01)
(52) U.S. Cl. .................... 8/405; 8/406; 8/407; 8/410; 8/411; 8/421; 8/594; 8/648; 132/202; 132/208
(58) Field of Classification Search .............. 8/405, 8/406, 407, 410, 411, 421, 594, 648; 132/202, 132/208
See application file for complete search history.

(56) References Cited

U.S. PATENT DOCUMENTS

| 2,261,002 A | 10/1941 | Ritter |
| 2,271,378 A | 1/1942 | Searle |
| 2,273,780 A | 2/1942 | Ditmar |
| 2,375,853 A | 5/1945 | Kirby et al. |
| 2,388,614 A | 11/1945 | Kirby et al. |
| 2,454,547 A | 11/1948 | Bock et al. |
| 2,798,053 A | 7/1957 | Brown |
| 2,851,424 A | 9/1958 | Switzer et al. |
| 2,923,692 A | 2/1960 | Ackerman et al. |
| 2,961,347 A | 11/1960 | Floyd |
| 2,979,465 A | 4/1961 | Parran et al. |
| 3,014,041 A | 12/1961 | Hausermann et al. |
| 3,206,462 A | 9/1965 | McCarty |
| 3,227,615 A | 1/1966 | Korden |
| 3,472,840 A | 10/1969 | Stone et al. |
| 3,632,559 A | 1/1972 | Matter et al. |
| 3,639,127 A | 2/1972 | Brooker et al. |
| 3,658,985 A | 4/1972 | Olson, Jr. et al. |
| 3,856,550 A | 12/1974 | Bens et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Vanlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,157,388 A | 6/1979 | Christiansen |
| 4,165,367 A | 8/1979 | Chakrabarti |
| 4,166,894 A | 9/1979 | Schaper |
| 4,172,887 A | 10/1979 | Vanlerberghe et al. |
| 4,185,087 A | 1/1980 | Morlino |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,237,243 A | 12/1980 | Quack et al. |
| 4,240,450 A | 12/1980 | Grollier et al. |
| 4,256,458 A | 3/1981 | Degen et al. |
| 4,277,581 A | 7/1981 | Vanlerberghe et al. |
| 4,381,919 A | 5/1983 | Jacquet et al. |
| 4,422,853 A | 12/1983 | Jacquet et al. |
| 4,445,521 A | 5/1984 | Grollier et al. |
| 4,509,949 A | 4/1985 | Huang et al. |

(Continued)

FOREIGN PATENT DOCUMENTS

AT 302 534 10/1972

(Continued)

OTHER PUBLICATIONS

CAS Abstract for JP 2000-136340—Chemical Abstracts Service; Database Accession No. 2000: 317079; XP-002269220, JP 2000136340 (Pentel Co., Ltd.), May 16, 2000.

(Continued)

*Primary Examiner*—Eisa Elhilo
(74) *Attorney, Agent, or Firm*—Finnegan, Henderson, Farabow, Garrett & Dunner, LLP

(57) ABSTRACT

The present disclosure relates to compositions comprising at least one soluble fluorescent dye and at least one compound comprising an acid functional group, and to processes using this composition.

It likewise relates to a method of using compositions comprising, in a cosmetically acceptable medium, at least one soluble fluorescent dye and at least one compound comprising an acid functional group for dyeing human keratin materials, such as artificially dyed and/or pigmented hair and dark skin, with a lightening effect.

56 Claims, No Drawings

U.S. PATENT DOCUMENTS

| | | |
|---|---|---|
| 4,517,174 A | 5/1985 | Jacquet et al. |
| 4,591,160 A | 5/1986 | Piragino |
| 4,608,250 A | 8/1986 | Jacquet et al. |
| 4,693,935 A | 9/1987 | Mazurek |
| 4,702,906 A | 10/1987 | Jacquet et al. |
| 4,719,099 A | 1/1988 | Grollier et al. |
| 4,719,282 A | 1/1988 | Nadolsky et al. |
| 4,728,571 A | 3/1988 | Clemens et al. |
| 4,761,273 A | 8/1988 | Grollier et al. |
| 4,781,724 A | 11/1988 | Wajaroff et al. |
| 4,823,985 A | 4/1989 | Grollier et al. |
| 4,839,166 A | 6/1989 | Grollier et al. |
| 4,948,579 A | 8/1990 | Jacquet et al. |
| 4,961,925 A | 10/1990 | Tsujino et al. |
| 4,972,037 A | 11/1990 | Garbe et al. |
| 4,996,059 A | 2/1991 | Grollier et al. |
| 5,009,880 A | 4/1991 | Grollier et al. |
| 5,057,311 A | 10/1991 | Kamegai et al. |
| 5,089,252 A | 2/1992 | Grollier et al. |
| 5,139,037 A | 8/1992 | Grollier et al. |
| 5,188,639 A | 2/1993 | Schultz et al. |
| 5,196,189 A | 3/1993 | Jacquet et al. |
| 5,275,808 A | 1/1994 | Murray et al. |
| 5,316,551 A | 5/1994 | Wenke |
| 5,356,438 A | 10/1994 | Kim et al. |
| 5,445,655 A | 8/1995 | Kuhn et al. |
| 5,635,461 A | 6/1997 | Onitsuka et al. |
| 5,708,151 A | 1/1998 | Möckli |
| 5,733,343 A | 3/1998 | Mockli |
| 5,744,127 A * | 4/1998 | Giuseppe et al. ............ 424/59 |
| 5,792,221 A | 8/1998 | Lagrange et al. |
| 5,830,446 A | 11/1998 | Berthiaume et al. |
| 5,833,997 A | 11/1998 | Mahieu et al. |
| 5,853,708 A | 12/1998 | Cauwet et al. |
| 5,873,494 A | 2/1999 | Dallas, Jr. |
| 5,958,392 A | 9/1999 | Grollier et al. |
| 5,961,667 A * | 10/1999 | Doehling et al. ............ 8/408 |
| 5,962,522 A | 10/1999 | Wacher et al. |
| 6,001,135 A | 12/1999 | Rondeau et al. |
| 6,106,577 A | 8/2000 | Audousset et al. |
| 6,120,780 A | 9/2000 | Dupuis et al. |
| 6,156,077 A | 12/2000 | Shibata et al. |
| 6,180,666 B1 | 1/2001 | Wacher et al. |
| 6,260,556 B1 | 7/2001 | Legrand et al. |
| 6,375,958 B1 | 4/2002 | Cauwet et al. |
| 6,391,062 B1 | 5/2002 | Vandenbossche et al. |
| 6,436,151 B2 | 8/2002 | Cottard et al. |
| 6,436,153 B2 * | 8/2002 | Rondeau ..................... 8/426 |
| 6,475,248 B2 | 11/2002 | Ohashi et al. |
| 6,570,019 B2 | 5/2003 | Pasquier et al. |
| 6,576,024 B1 | 6/2003 | Lang et al. |
| 6,592,630 B2 | 7/2003 | Matsunaga et al. |
| 6,616,709 B2 | 9/2003 | Ohashi et al. |
| 6,712,861 B2 | 3/2004 | Rondeau |
| 2001/0010812 A1 | 8/2001 | Chevalier et al. |
| 2001/0023514 A1 | 9/2001 | Cottard et al. |
| 2001/0023515 A1 | 9/2001 | Cottard et al. |
| 2001/0031270 A1 | 10/2001 | Douin et al. |
| 2001/0034914 A1 | 11/2001 | Saunier et al. |
| 2001/0054206 A1* | 12/2001 | Matsunaga et al. ............ 8/405 |
| 2001/0055580 A1 | 12/2001 | Belli et al. |
| 2002/0004956 A1 | 1/2002 | Rondeau |
| 2002/0012681 A1 | 1/2002 | George et al. |
| 2002/0026676 A1 | 3/2002 | Ohashi et al. |
| 2002/0046431 A1 | 4/2002 | Laurent et al. |
| 2002/0046432 A1 | 4/2002 | Rondeau |
| 2002/0088063 A1 | 7/2002 | Ohashi et al. |
| 2002/0131941 A1 | 9/2002 | Habeck et al. |
| 2002/0176836 A9 | 11/2002 | Belli et al. |
| 2002/0176875 A9 | 11/2002 | Douin et al. |
| 2003/0000023 A9 | 1/2003 | Rondeau |
| 2003/0019052 A1 | 1/2003 | Pratt |
| 2003/0019053 A9 | 1/2003 | Rondeau |
| 2003/0055268 A1 | 3/2003 | Pasquier et al. |
| 2003/0074747 A1 | 4/2003 | Vuarier et al. |
| 2003/0124079 A1 | 7/2003 | Mougin et al. |
| 2003/0131424 A1 | 7/2003 | Audousset et al. |
| 2004/0019981 A1 | 2/2004 | Cottard et al. |
| 2004/0034945 A1 | 2/2004 | Javet et al. |
| 2004/0037796 A1 | 2/2004 | Cottard et al. |
| 2004/0049860 A1 | 3/2004 | Cottard et al. |
| 2004/0105830 A1 | 6/2004 | Boswell et al. |
| 2004/0141943 A1 | 7/2004 | Mougin et al. |
| 2004/0148711 A1 | 8/2004 | Rondeau |
| 2004/0205901 A1 | 10/2004 | Cottard et al. |
| 2004/0258641 A1 | 12/2004 | Plos et al. |
| 2005/0005368 A1 | 1/2005 | Plos et al. |
| 2005/0005369 A1 | 1/2005 | Plos et al. |
| 2005/0008593 A1 | 1/2005 | Plos et al. |
| 2005/0028301 A1 | 2/2005 | Pastore |
| 2005/0144741 A1 | 7/2005 | Lang et al. |

FOREIGN PATENT DOCUMENTS

| | | |
|---|---|---|
| CA | 1255603 | 6/1989 |
| CH | 487 231 | 3/1970 |
| DE | 33 133 32 | 10/1984 |
| DE | 196 46 804 A1 | 5/1997 |
| DE | 199 23 438 A1 | 11/2000 |
| DE | 199 26 377 A1 | 12/2000 |
| DE | 100 29 441 A1 | 1/2002 |
| DE | 101 41 683 A1 | 6/2003 |
| DE | 101 48 844 A1 | 10/2003 |
| EP | 0 087 060 B1 | 8/1983 |
| EP | 0 095 238 A2 | 11/1983 |
| EP | 0 080 976 B1 | 9/1986 |
| EP | 0 173 109 | 10/1989 |
| EP | 0 370 470 B1 | 5/1990 |
| EP | 0 412 704 B1 | 2/1991 |
| EP | 0 412 707 B1 | 2/1991 |
| EP | 0 445 342 B1 | 9/1991 |
| EP | 0 486 135 B1 | 5/1992 |
| EP | 0 122 324 B2 | 2/1993 |
| EP | 0 337 354 B1 | 2/1994 |
| EP | 0 582 152 B1 | 2/1994 |
| EP | 0 395 282 | 3/1995 |
| EP | 0 503 853 | 5/1996 |
| EP | 0 714 954 A2 | 6/1996 |
| EP | 0 733 355 A2 | 9/1996 |
| EP | 0 808 150 | 5/1997 |
| EP | 0 815 828 B1 | 6/1999 |
| EP | 0 970 684 A1 | 1/2000 |
| EP | 1 023 891 B1 | 8/2000 |
| EP | 1 142 559 | 4/2001 |
| EP | 1 099 437 | 5/2001 |
| EP | 1 132 076 A1 | 9/2001 |
| EP | 1 133 977 A2 | 9/2001 |
| EP | 1 191 041 A2 | 3/2002 |
| FR | 1492597 | 9/1966 |
| FR | 1583363 | 10/1969 |
| FR | 2077143 | 10/1971 |
| FR | 2080759 | 11/1971 |
| FR | 2103210 | 7/1972 |
| FR | 2162025 | 7/1973 |
| FR | 2190406 | 2/1974 |
| FR | 2252840 | 6/1975 |
| FR | 2270846 | 12/1975 |
| FR | 2280361 | 2/1976 |
| FR | 2316271 | 1/1977 |
| FR | 2320330 | 3/1977 |
| FR | 2336434 | 7/1977 |
| FR | 2368508 | 5/1978 |
| FR | 2383660 | 10/1978 |
| FR | 2393573 | 1/1979 |

| | | |
|---|---|---|
| FR | 2411219 | 7/1979 |
| FR | 2416723 | 9/1979 |
| FR | 2470596 | 6/1981 |
| FR | 2505348 | 11/1982 |
| FR | 2519863 | 7/1983 |
| FR | 2542997 | 9/1984 |
| FR | 2586913 | 3/1987 |
| FR | 2589476 | 5/1987 |
| FR | 2598611 | 11/1987 |
| FR | 2692572 | 6/1992 |
| FR | 2741261 | 5/1997 |
| FR | 2 773 470 | 7/1999 |
| FR | 2773864 | 7/1999 |
| FR | 2797877 | 3/2001 |
| FR | 2800612 | 5/2001 |
| FR | 2811993 | 1/2002 |
| FR | 2820032 | 8/2002 |
| FR | 2830189 | 4/2003 |
| GB | 746864 | 3/1956 |
| GB | 759385 | 10/1956 |
| GB | 1214394 | 1/1970 |
| GB | 1546809 | 5/1979 |
| GB | 1554331 | 10/1979 |
| JP | 48-17362 | 5/1973 |
| JP | 54-86521 | 7/1979 |
| JP | 2-200612 | 8/1990 |
| JP | 6-128128 | 5/1994 |
| JP | 6-183935 | 7/1994 |
| JP | 6-227954 | 8/1994 |
| JP | 8-183716 | 7/1996 |
| JP | 8-208448 | 8/1996 |
| JP | 8-259426 | 10/1996 |
| JP | 9-183714 | 7/1997 |
| JP | 10-23629 | 9/1998 |
| JP | 11-021214 | 1/1999 |
| JP | 11-60453 | 3/1999 |
| JP | 11-343218 | 12/1999 |
| JP | 2000-01417 | 1/2000 |
| JP | 2000-86472 | 3/2000 |
| JP | 2000-505841 | 5/2000 |
| JP | 2001-172120 | 6/2001 |
| JP | 2001-220330 | 8/2001 |
| JP | 2001-226217 | 8/2001 |
| JP | 2001-261534 | 9/2001 |
| JP | 2001-261536 | 9/2001 |
| JP | 2001-294519 | 10/2001 |
| JP | 2001-302473 | 10/2001 |
| JP | 2001-516701 | 10/2001 |
| JP | 2001-516705 | 10/2001 |
| JP | 2001-516706 | 10/2001 |
| JP | 2001-516707 | 10/2001 |
| JP | 2002-12523 | 1/2002 |
| JP | 2002-12530 | 1/2002 |
| JP | 2002-47151 | 2/2002 |
| JP | 2002-226338 | 8/2002 |
| JP | 2002-249419 | 9/2002 |
| JP | 2002-326911 | 11/2002 |
| JP | 2003-55177 | 2/2003 |
| JP | 2004-059468 | 2/2004 |
| JP | 2004-307494 | 11/2004 |
| JP | 2004-307495 | 11/2004 |
| WO | WO 93/11103 | 6/1993 |
| WO | WO 93/23009 | 11/1993 |
| WO | WO 93/23446 | 11/1993 |
| WO | WO 94/02022 | 2/1994 |
| WO | WO 95/00578 | 1/1995 |
| WO | WO 95/01772 | 1/1995 |
| WO | WO 95/15144 | 6/1995 |
| WO | WO 97/18795 | 5/1997 |
| WO | WO 99/12846 | 3/1999 |
| WO | WO 99/13822 | 3/1999 |
| WO | WO 99/13823 | 3/1999 |
| WO | WO 99/13824 | 3/1999 |
| WO | WO 99/13828 | 3/1999 |
| WO | WO 99/13841 | 3/1999 |
| WO | WO 99/13844 | 3/1999 |
| WO | WO 99/13845 | 3/1999 |
| WO | WO 99/13846 | 3/1999 |
| WO | WO 99/13847 | 3/1999 |
| WO | WO 99/13849 | 3/1999 |
| WO | WO 99/20235 A1 | 4/1999 |
| WO | WO 99/36045 | 7/1999 |
| WO | WO 00/68282 | 11/2000 |
| WO | WO 00/71085 A2 | 11/2000 |
| WO | WO 01/43714 A1 | 6/2001 |
| WO | WO 01/62759 A1 | 8/2001 |
| WO | WO 01/78669 | 10/2001 |
| WO | WO 02/32386 A2 | 4/2002 |
| WO | WO 02/38115 A1 | 5/2002 |
| WO | WO 02/39964 A1 | 5/2002 |
| WO | WO 02/45673 A2 | 6/2002 |
| WO | WO 02/58646 A1 | 8/2002 |
| WO | WO 02/58647 A1 | 8/2002 |
| WO | WO 02/74270 | 9/2002 |
| WO | WO 03/22232 A2 | 3/2003 |
| WO | WO 03/28685 A1 | 4/2003 |
| WO | WO 03/029359 | 4/2003 |

OTHER PUBLICATIONS

Co-pending U.S. Appl. No. 10/814,334, filed Apr. 1, 2004.
Co-pending U.S. Appl. No. 10/814,333, filed Apr. 1, 2004.
Co-pending U.S. Appl. No. 10/814,305, filed Apr. 1, 2004.
Co-pending U.S. Appl. No. 10/814,300, filed Apr. 1, 2004.
Co-pending U.S. Appl. No. 10/814,335, filed Apr. 1, 2004.
Co-pending U.S. Appl. No. 10/814,428, filed Apr. 1, 2004.
Co-pending U.S. Appl. No. 10/490,869, filed Apr. 1, 2004.
Co-pending U.S. Appl. No. 10/814,236, filed Apr. 1, 2004.
Co-pending U.S. Appl. No. 10/814,338, filed Apr. 1, 2004.
Co-pending U.S. Appl. No. 10/814,337, filed Apr. 1, 2004.
Co-pending U.S. Appl. No. 10/814,585, filed Apr. 1, 2004.
Co-pending U.S. Appl. No. 10/742,995, filed Dec. 23, 2003.
Co-pending U.S. Appl. No. 10/814,336, filed Apr. 1, 2004.
English Language Derwent Abstract of DE 100 29 441.
English Language Derwent Abstract of DE 101 41 683.
English Language Derwent Abstract of DE 101 48 844.
English Language Derwent Abstract of DE 199 23 438.
English Language Derwent Abstract of DE 199 26 377.
English Language Derwent Abstract of EP 0 080 976.
English Language Derwent Abstract of EP 0 087 060.
English Language Derwent Abstract of EP 1 023 891.
English Language Derwent Abstract of EP 1 099 437.
English Language Derwent Abstract of FR 2,800,612.
English Language Abstract of FR 2 598 476 (EP 0 225 261) from EPO website.
English Language Derwent Abstract of JP 10-23629.
English Language Derwent Abstract of JP 11-060453.
English Language Derwent Abstract of JP 11-21214.
English Language Derwent Abstract of JP 2000-1417.
English Language Derwent Abstract of JP 2000-086472.
English Language Derwent Abstract of JP 2001-172120.
English Language Derwent Abstract of JP 2001-261534.
English Language Derwent Abstract of JP 2001-294519.
English Language Derwent Abstract of JP 2001-516701.
English Language Derwent Abstract of JP 2001-516706.
English Language Derwent Abstract of JP 2001-516707.
English Language Derwent Abstract of JP 2002-226338.
English Language Abstract of JP 2002-249419 from Japio database.
English Language Derwent Abstract of JP 2004-59468.
English Language Derwent Abstract of JP 2-200612.
English Language Derwent Abstract of JP 54-086521.
English Language Derwent Abstract of JP 6-183935.
English Language Derwent Abstract of JP 6-227954.
English Language Derwent Abstract of JP 8-183716.
English Language Derwent Abstract of JP 8-208448.
English Language Derwent Abstract of JP 8-259426.

French Search Report for French Patent Application No. FR 03/04021, priority document for U.S. Appl. No. 10/814,337, Dec. 8, 2003.
French Search Report for French Patent Application No. FR 03/04022, priority document for co-pending U.S. Appl. No. 10/814,336, Nov. 20, 2003.
French Search Report for French Patent Application No. FR 03/04024, priority document for co-pending U.S. Appl. No. 10/814,585, Dec. 8, 2003.
French Search Report for French Patent Application No. FR 03/04026, priority document for co-pending U.S. Appl. No. 10/814,335, Nov. 21, 2003.
French Search Report for French Patent Application No. FR 03/04027, priority document for co-pending U.S. Appl. No. 10/814,428, Nov. 28, 2003.
French Search Report for French Patent Application No. FR 03/04028, priority document for co-pending U.S. Appl. No. 10/814,236, Nov. 25, 2003.
French Search Report for French Patent Application No. FR 03/04029, priority document for co-pending U.S. Appl. No. 10/814,430, Feb. 5, 2004.
French Search Report for French Patent Application No. FR 03/04030, priority document for co-pending U.S. Appl. No. 10/814,300, Nov. 27, 2003.
French Search Report for French Patent Application No. FR 03/04031, priority document for co-pending U.S. Appl. No. 10/814,333, Jan. 8, 2004.
French Search Report for French Patent Application No. FR 03/04033, priority document for co-pending U.S. Appl. No. 10/814,334, Nov. 28, 2003.
French Search Report for French Patent Application No. FR 03/04034, priority document for co-pending U.S. Appl. No. 10/814,338, Feb. 17, 2004.
French Search Report for French Patent Application No. FR 03/04035, priority document for co-pending U.S. Appl. No. 10/814,305, Feb. 5, 2004.
French Search Report for French Patent Application No. FR 02/16669, priority document for co-pending U.S. Appl. No. 10/742,995, Aug. 6, 2003.
International Search Report for PCT Application No. PCT/FR 02/03252, (for co-pending U.S. Appl. No. 10/490,869), Jan. 20, 2003.
Office Action mailed Mar. 27, 2006 in co-pending U.S. Appl. No. 10/814,334.
Office Action dated Mar. 15, 2006 in co-pending U.S. Appl. No. 10/814,337.
Office Action mailed Nov. 17, 2005 in co-pending U.S. Appl. No. 10/814,336.
Office Action mailed Nov. 3, 2005 in co-pending U.S. Appl. No. 10/490,869.
Office Action mailed Nov. 2, 2005 in co-pending U.S. Appl. No. 10/814,338.
Office Action mailed Nov. 2, 2005 in co-pending U.S. Appl. No. 10/742,995.
Jacobi, Otto and Jacobi, Gertrud, "Investigation into the reciprocal action of cosmetics and the biosphere of the stratum corneuum of the skin," *Cosmetics and Toiletries*, 91:25-32 (Jan. 1976).
Science Des Traitements Capillaires [Hair Treatment Sciences] by Charles Zviak, 1988, published by Masson, pp. 215 and 278.
M. Schlossmann, "The Chemistry and Manufacture of Cosmetics Formulating," 2(3):522-526 (2000).
C. D. Williams et al., "Chemistry and Technology of the Cosmetics and Toiletries Industry," ed. 2, pp. 77-78 (1996).
Yuuki Kagoubutsu Jilen (Dictionary of Organic Compounds), Kodansha Ltd., Aug. 10, 2002, p. 908.
G. Fonnum, J. Bakke and Fk. Hansen—Colloid Polym. Sci 271, 380-389 (1993).
Zviak, C., The Science of Hair Care, pp. 215 and 278 (1986).
English language Derwent Abstract of JP 2001-302473.
English language Derwent Abstract of JP 2002-326911.
English language Derwent Abstract of JP 9-183714.
English language Derwent Abstract of FR 2 773 470.
Mishra, J.K. et al. "Synthesis of some bischromophoric dyes containing nonabsorbing flexible bridge," Indian Journal of Chemistry, vol. 31B, pp. 118-112, Feb. 1992.
Office Action mailed Apr. 6, 2006 in co-pending U.S. Appl. No. 10/742,995.
Office Action mailed Aug. 24, 2006 in co-pending U.S. Appl. No. 10/814,305.
Office Action mailed Aug. 28, 2006 in co-pending U.S. Appl. No. 10/814,236.
Office Action mailed Aug. 28, 2006 in co-pending U.S. Appl. No. 10/814,300.
Office Action mailed Jul. 7, 2006, in co-pending U.S. Appl. No. 10/814,585.
Office Action mailed Jun. 21, 2006, in co-pending U.S. Appl. No. 10/814,336.
Office Action mailed Mar. 15, 2006 in co-pending U.S. Appl. No. 10/814,305.
Office Action mailed Mar. 23, 2006 in co-pending U.S. Appl. No. 10/814,300.
Office Action mailed Mar. 24, 2006 in co-pending U.S. Appl. No. 10/814,236.
Office Action mailed May 18, 2006, in co-pending U.S. Appl. No. 10/814,333.
Office Action mailed May 25, 2006, in co-pending U.S. Appl. No. 10/814,335.
Office Action mailed May 26, 2006, in co-pending U.S. Appl. No. 10/490,869.
Office Action mailed May 30, 2006, in co-pending U.S. Appl. No. 10/814,338.

* cited by examiner

COMPOSITION FOR DYEING HUMAN KERATIN MATERIALS, COMPRISING AT LEAST ONE FLUORESCENT DYE AND AT LEAST ONE COMPOUND COMPRISING AN ACID FUNCTIONAL GROUP AND PROCESSES THEREFOR

This application claims benefit of U.S. Provisional Application No. 60/468,078, filed May 6, 2003.

The present disclosure relates to compositions comprising at least one fluorescent dye and at least one compound comprising an acid functional group, and also to processes and a device for using these compositions. The disclosure further relates to the use of compositions comprising at least one fluorescent dye and at least one compound comprising an acid functional group for dyeing with a lightening effect human keratin materials, such as keratin fibers, e.g., artificially dyed and/or pigmented hair, and also dark skin.

It is common for individuals with dark skin to wish to lighten their skin and for this purpose to use cosmetic or dermatological compositions containing bleaching agents.

The substances most commonly used as bleaching agents are hydroquinone and its derivatives, kojic acid and its derivatives, azelaic acid, and arbutin and its derivatives, alone or in combination with other active agents.

However, these agents are not without their drawbacks. In particular, they may need to be used for a long time and in large amounts in order to obtain a bleaching effect on the skin. No immediate effect is observed on applying compositions comprising them.

In addition, hydroquinone and its derivatives may be used in an amount that is effective to produce a visible bleaching effect. In particular, hydroquinone is known for its cytotoxicity towards melanocytes.

Moreover, kojic acid and its derivatives have the drawback of being expensive and consequently of not being able to be used in a large amount in products for commercial mass distribution.

There is thus still a need for cosmetic compositions that may allow a lighter, uniform, homogeneous skin tone of natural appearance to be obtained, these compositions having satisfactory transparency after application to the skin.

In the field of haircare, there are mainly two major types of hair dyeing.

The first is semi-permanent dyeing or direct dyeing, which uses dyes capable of giving the hair's natural color a more or less pronounced modification that may withstand shampooing several times. These dyes are known as direct dyes and may be used in two different ways. The colorations may be performed by applying the composition comprising at least one direct dye directly to the keratin fibers, or by applying a mixture, prepared extemporaneously, of a composition comprising at least one direct dye with a composition comprising at least one oxidizing bleaching agent, for example an aqueous hydrogen peroxide solution. As used herein, such a process is termed "lightening direct dyeing".

The second is permanent dyeing or oxidation dyeing. This is performed with "oxidation" dye precursors, which are colorless or weakly colored compounds which, once mixed with oxidizing products, at the time of use, can give rise to colored compounds and dyes via a process of oxidative condensation. It is possible to combine at least one direct dye with at least one oxidation base and at least one coupler in order to neutralize or attenuate the shades with too much of a red, orange, or golden glint, or, on the contrary, to accentuate these red, orange, or golden glints.

Among the available direct dyes, nitrobenzene direct dyes may not be sufficiently strong, and indoamines, quinone dyes, and natural dyes may have a low affinity for keratin fibers and consequently lead to colorations that are not sufficiently fast with respect to the various treatments to which the fibers may be subjected, for example with respect to shampooing.

In addition, there is a need to obtain a lightening effect on human keratin fibers. This lightening is conventionally obtained via a process of bleaching the melanins of the hair via an oxidizing system generally comprising hydrogen peroxide optionally combined with persalts. This bleaching system, however, may have the drawback of degrading the keratin fibers and of impairing their cosmetic properties.

The present disclosure aims to solve the problems mentioned above and to propose a composition that provides at least one of good dyeing affinity for keratin materials, such as keratin fibers, good resistance properties with respect to external agents, for example with respect to shampooing, and also may make it possible to obtain lightening without impairing the treated material, such as the keratin fiber.

It has thus been found, surprisingly and unexpectedly, that the use of at least one fluorescent dye, in the presence of at least one compound comprising an acid functional group, may allow these objectives to be achieved.

One embodiment disclosed herein is thus a composition comprising, in a cosmetically acceptable medium, at least one fluorescent dye that is soluble in the medium and at least one compound comprising an acid functional group, with a molecular weight of less than 500 g/mol, chosen from mineral compounds and organic compounds comprising at least one of carboxylic functional groups, sulphonic functional groups, linear or branched, saturated or unsaturated, hydrocarbon-based radicals comprising 1 to 30 carbon atoms, and aromatic radicals comprising 6 to 30 carbon atoms, the hydrocarbon-based radicals optionally being substituted with at least one entity chosen from hetero atoms, groups comprising at least one hetero atom, and halogen atoms, and the hydrocarbon-based radicals optionally being interrupted with at least one entity chosen from hetero atoms and groups comprising at least one hetero atom; the composition not comprising, as the at least one fluorescent dye, 2-[2-(4-dialkylamino)phenylethenyl]-1-alkylpyridinium in which the alkyl radical of the pyridinium nucleus is chosen from methyl and ethyl radicals, the alkyl radical of the benzene nucleus represents a methyl radical, and the counterion is a halide.

Another embodiment concerns a process for dyeing human keratin fibers with a lightening effect, comprising:
a) applying a composition as disclosed herein to the fibers, for a time that is sufficient to develop the desired coloration and lightening,
b) optionally rinsing the fibers,
c) optionally washing the fibers with shampoo and optionally rinsing the fibers, and
d) drying the fibers or leaving the fibers to dry.

Another embodiment relates to the use, for dyeing human keratin materials with a lightening effect, of a composition comprising, in a cosmetically acceptable medium, at least one fluorescent dye that is soluble in the medium and at least one compound comprising an acid functional group, with a molecular weight of less than 500 g/mol, chosen from mineral compounds and organic compounds comprising at least one of carboxylic functional groups, sulphonic functional groups, linear or branched, saturated or unsaturated, hydrocarbon-based radicals comprising 1 to 30 carbon atoms, and aromatic radicals comprising 6 to 30 carbon atoms, the hydrocarbon-based radicals optionally being substituted with at least one entity chosen from hetero atoms, groups comprising at least one hetero atom, and halogen atoms, and the hydrocarbon-based radicals optionally being interrupted with at least one entity chosen from hetero atoms and groups comprising at least one hetero atom.

Yet another embodiment according to the present disclosure is a multi-compartment device for dyeing and lightening keratin fibers, comprising at least one compartment comprising a composition disclosed herein, and at least one other compartment comprising a composition comprising at least one oxidizing agent.

The compositions disclosed herein may allow better fixing of the at least one fluorescent dye onto the keratin materials, which is reflected by an increased fluorescent effect and a lightening effect that may be greater than that obtained with the fluorescent dye used alone.

Better resistance of the result with respect to washing and/or shampooing may also be found.

However, other characteristics and advantages of the present disclosure will emerge more clearly on reading the description and the examples that follow.

Unless otherwise indicated, the limits of the ranges of values that are given in the description are included in these ranges.

As has been mentioned previously, the compositions disclosed herein comprise at least one fluorescent dye and at least one compound comprising an acid functional group.

As used herein, the term "fluorescent dye" means a dye which is a molecule that colors by itself, and thus absorbs light in the visible spectrum and possibly in the ultraviolet spectrum (wavelengths ranging from 360 to 760 nanometers), but which, in contrast with a standard dye, converts the absorbed energy into fluorescent light of a longer wavelength emitted in the visible region of the spectrum.

A fluorescent dye as disclosed herein is to be differentiated from an optical brightener. Optical brighteners, which are also known as brighteners, fluorescent brighteners, fluorescent brightening agents, fluorescent whitening agents, whiteners, and fluorescent whiteners, are colorless transparent compounds, which do not dye because they do not absorb light in the visible region, but only in the ultraviolet region (wavelengths ranging from 200 to 400 nanometers), and convert the absorbed energy into fluorescent light of a longer wavelength emitted in the visible region of the spectrum. The color impression is then generated by purely fluorescent light that is predominantly blue (wavelengths ranging from 400 to 500 nanometers).

Finally, the at least one fluorescent dye used in the composition is soluble in the medium of the composition. The at least one fluorescent dye differs therein from a fluorescent pigment, which itself is insoluble in the medium of the composition.

The at least one fluorescent dye used herein, which is optionally neutralized, is soluble in the medium of the composition to at least 0.001 g/l, for example to at least 0.5 g/l, or to at least 1 g/l, at a temperature ranging from 15° C. to 25°. According to another embodiment, the at least one fluorescent dye is soluble to at least 5 g/l at a temperature ranging from 15° C. to 25° C.

Moreover, according to one embodiment, the composition does not comprise, as the at least one fluorescent dye, a 2-[2-(4-dialkylamino)phenylethenyl]-1-alkyl pyridinium in which the alkyl radical of the pyridinium nucleus is chosen from methyl and ethyl radicals, the alkyl radical of the benzene nucleus represents a methyl radical, and the counterion is a halide.

In accordance with another embodiment, the composition does not comprise, as the at least one fluorescent dye, any compound chosen from azo, azomethine, and methine monocationic heterocyclic fluorescent dyes.

The at least one fluorescent dye which may be used herein may be chosen from dyes in the orange range.

The at least one fluorescent dye disclosed herein may give a reflectance maximum that is in the wavelength range from 500 to 650 nanometers, for example in the wavelength range from 550 to 620 nanometers.

The fluorescent dyes used in the context of certain embodiments are, in certain cases, known compounds.

As examples of fluorescent dyes that may be used, mention may be made of the fluorescent dyes belonging to the following families: naphthalimides; cationic coumarins; non-cationic coumarins; xanthenodiquinolizines (such as sulphorhodamines); azaxanthenes; naphtholactams; azlactones; oxazines; thiazines; dioxazines; azo, azomethine, and methine polycationic fluorescent dyes; and mixtures thereof, and for example to the following families: naphthalimides; cationic coumarins; non-cationic coumarins; azaxanthenes; naphtholactams; azlactones; oxazines; thiazines; dioxazines; azo, azomethine, and methine polycationic fluorescent dyes; and mixtures thereof.

The following may be mentioned among the above dyes: Brilliant Yellow B6GL sold by the company Sandoz and having the following structure:

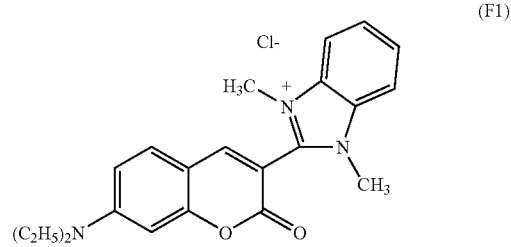

(F1)

Basic Yellow 2, or Auramine O, sold by the companies Prolabo, Aldrich, and Carlo Erba and having the following structure:

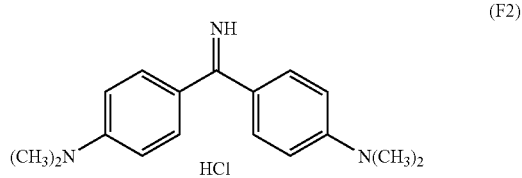

(F2)

4,4'-(imidocarbonyl)bis(N,N-dimethylaniline)monohydrochloride—CAS number 2465-27-2.

Mention may also be made of the compounds having the following formula:

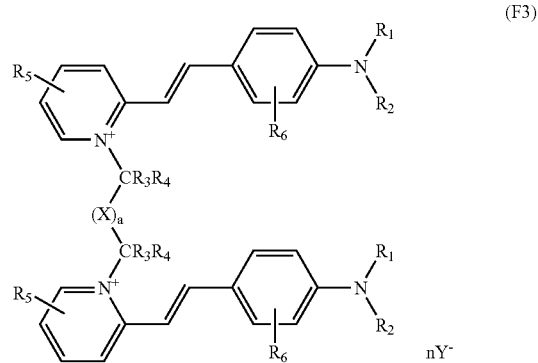

(F3)

in which:

$R_1$ and $R_2$, which may be identical or different, are chosen from:
  hydrogen atoms;
  linear or branched alkyl radicals comprising 1 to 10 carbon atoms, such as 1 to 4 carbon atoms, which may optionally be interrupted with at least one entity chosen from hetero atoms and groups comprising at least one hetero atom, and which may optionally be substituted with at least one entity chosen from hetero atoms, groups comprising at least one hetero atom, and halogen atoms;
  aryl and arylalkyl radicals, the aryl groups comprising 6 carbon atoms and the alkyl groups comprising 1 to 4 carbon atoms; wherein the aryl groups are optionally substituted with at least one linear or branched alkyl radical comprising 1 to 4 carbon atoms, wherein said at least one alkyl radical is optionally interrupted with at least one entity chosen from hetero atoms and groups comprising at least one hetero atom and is optionally substituted with at least one entity chosen from hetero atoms, groups comprising at least one hetero atom, and halogen atoms;
  $R_1$ and $R_2$ may optionally be linked so as to form a heterocycle with the nitrogen atom to which they are attached and may comprise at least one other hetero atom, the heterocycle optionally being substituted with at least one linear or branched alkyl radical, for example an alkyl radical comprising 1 to 4 carbon atoms, said alkyl radical optionally being interrupted with at least one entity chosen from hetero atoms and groups comprising at least one hetero atom and optionally being substituted with at least one entity chosen from hetero atoms, groups comprising at least one hetero atom, and halogen atoms;
  $R_1$ or $R_2$ may optionally form a heterocycle comprising the nitrogen atom to which they are attached and one of the carbon atoms of the phenyl group comprising the nitrogen atom;

$R_3$ and $R_4$, which may be identical or different, are chosen from hydrogen atoms and alkyl radicals comprising 1 to 4 carbon atoms;

$R_5$, which may be identical or different, is chosen from hydrogen atoms, halogen atoms, and linear or branched alkyl radicals comprising 1 to 4 carbon atoms, optionally interrupted with at least one hetero atom;

$R_6$, which may be identical or different, is chosen from hydrogen atoms; halogen atoms; and linear or branched alkyl radicals comprising 1 to 4 carbon atoms, wherein said alkyl radicals are optionally substituted with at least one entity chosen from hetero atoms, groups comprising at least one hetero atom, and halogen atoms, and are optionally interrupted with at least one entity chosen from hetero atoms and groups comprising at least one heteroatom;

X is chosen from:
  linear or branched alkyl radicals comprising 1 to 14 carbon atoms and alkenyl radicals comprising 2 to 14 carbon atoms, wherein said alkyl radicals and said alkenyl radicals are optionally interrupted with at least one entity chosen from hetero atoms and groups comprising at least one hetero atom and are optionally substituted with at least one entity chosen from hetero atoms, groups comprising at least one hetero atom, and halogen atoms;
  5- or 6-membered heterocyclic radicals optionally substituted with at least one entity chosen from linear or branched alkyl radicals comprising 1 to 14 carbon atoms, optionally substituted with at least one hetero atom;
  linear or branched aminoalkyl radicals comprising 1 to 4 carbon atoms, optionally substituted with at least one hetero atom; and
  halogen atoms;
  fused or non-fused, aromatic or diaromatic radicals, optionally separated with at least one alkyl radical comprising 1 to 4 carbon atoms, the aromatic or diaromatic radicals optionally being substituted with at least one of halogen atoms and alkyl radicals comprising 1 to 10 carbon atoms, said alkyl radicals comprising 1 to 10 carbon atoms being optionally substituted with at least one entity chosen from hetero atoms and groups bearing at least one hetero atom, and being optionally interrupted with at least one entity chosen from hetero atoms and groups bearing at least one hetero atom; and
  dicarbonyl radicals;

wherein the group X optionally comprises at least one cationic charge;

a is chosen from 0 and 1;

$Y^-$, which may be identical or different, is chosen from organic and mineral anions; and n is an integer at least equal to 2 and at most equal to the number of cationic charges present in the at least one fluorescent dye compound.

The term "hetero atom" as used herein means an atom chosen from oxygen and nitrogen atoms.

Among the groups comprising such atoms that may be mentioned, inter alia, are hydroxyl, alkoxy, carbonyl, amino, ammonium, amido (—N—CO—), and carboxyl (e.g., —O—CO— and —CO—O—) groups.

As regards the alkenyl groups, they may comprise at least one unsaturated carbon-carbon bonds (e.g., —C=C—), such as one carbon-carbon double bond.

In this general formula, the radicals $R_1$ and $R_2$, which may be identical or different, may, for example, be chosen from:
  hydrogen atoms;
  alkyl radicals comprising 1 to 10 carbon atoms, for example 1 to 6 carbon atoms and for example 1 to 4 carbon atoms, optionally interrupted with an oxygen atom and optionally substituted with at least one entity chosen from hydroxyl radicals, amino radicals, ammonium radicals, chlorine atoms, and fluorine atoms;
  benzyl and phenyl radicals optionally substituted with at least one of alkyl and alkoxy radicals comprising 1 to 4 carbon atoms, for example 1 or 2 carbon atoms;
  together with the nitrogen atom to which they are attached, heterocyclic radicals of the pyrrolo, pyrrolidino, imidazolino, imidazolo, imidazolium, pyrazolino, piperazino, morpholino, morpholo, pyrazolo, and triazolo types, optionally substituted with at least one linear or branched alkyl radical comprising 1 to 4 carbon atoms, said at least one alkyl radical being optionally interrupted and/or substituted with at least one entity chosen from nitrogen atoms, oxygen atoms, and groups bearing at least one atom chosen from nitrogen and oxygen atoms.

As regards the abovementioned amino and ammonium radicals, the radicals borne by the nitrogen atom may be identical or different and may for example be chosen from hydrogen atoms, $C_1$–$C_{10}$ (such as $C_1$–$C_4$) alkyl radicals, and arylalkyl radicals in which, for example, the aryl groups comprise 6 carbon atoms and the alkyl groups comprise 1 to 10 carbon atoms, for example 1 to 4 carbon atoms.

According to one embodiment disclosed herein, the radicals $R_1$ and $R_2$, which may be identical or different, are chosen from hydrogen atoms; linear or branched $C_1$–$C_6$ alkyl radicals; $C_2$–$C_6$ alkyl radicals substituted with at least one hydroxyl radical; $C_2$–$C_6$ alkyl radicals comprising at least one group chosen from amino and ammonium groups; $C_2$–$C_6$ chloroalkyl radicals; $C_2$–$C_6$ alkyl radicals interrupted with at least one entity chosen from oxygen atoms and groups comprising an oxygen atom (for example ester); aromatic radicals, for instance phenyl, benzyl, and 4-methylphenyl radicals; and heterocyclic radicals such as pyrrolo, pyrrolidino, imidazolo, imidazolino, imidazolium, piperazino, morpholo, morpholino, pyrazolo, and triazolo radicals, optionally substituted with at least one radical chosen from $C_1$–$C_6$ alkyl and aromatic radicals.

In certain embodiments, the radicals $R_1$ and $R_2$, which may be identical or different, are chosen from hydrogen atoms, linear or branched $C_1$–$C_6$ alkyl radicals such as methyl, ethyl, n-butyl, and n-propyl radicals; 2-hydroxyethyl; at least one radical chosen from alkyltrimethylammonium and alkyltriethylammonium radicals, the alkyl radicals being linear $C_2$–$C_6$ alkyl radicals; at least one radical chosen from (di)alkylmethylamino and (di)alkylethylamino radicals, the alkyl radicals being linear $C_1$–$C_6$ alkyl radicals; —$CH_2CH_2Cl$; —$(CH_2)_n$—$OCH_3$ and —$(CH_2)_n$—$OCH_2CH_3$ with n being an integer ranging from 2 to 6; —$CH_2CH_2$—$OCOCH_3$; and —$CH_2CH_2COOCH_3$.

For example, the radicals $R_1$ and $R_2$, which may be identical or different, and are, for example identical, are chosen from methyl radicals and ethyl radicals.

The radicals $R_1$ and $R_2$, which may be identical or different, may also be chosen from heterocyclic radicals of the pyrrolidino, 3-aminopyrrolidino, 3-(dimethyl)-aminopyrrolidino, 3-(trimethyl)aminopyrrolidino, 2,5-dimethylpyrrolo, 1H-imidazolo, 4-methylpiperazino, 4-benzylpiperazino, morpholo, 3,5-(tert-butyl)-1H-pyrazolo, 1H-pyrazolo and 1H-1,2,4-triazolo types.

The radicals $R_1$ and $R_2$, which may be identical or different, may also represent and be linked so as to form a heterocycle of formula (I) or (II) below:

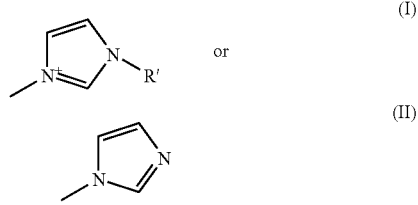

in which R' is chosen from hydrogen atoms, $C_1$–$C_3$ alkyl radicals, —$CH_2CH_2OH$, and —$CH_2CH_2OCH_3$.

In accordance with another embodiment, $R_5$, which may be identical or different, is chosen from hydrogen atoms, fluorine atoms, chlorine atoms, and linear or branched alkyl radicals comprising 1 to 4 carbon atoms optionally interrupted with at least one atom chosen from oxygen and nitrogen atoms.

It is pointed out that the substituent $R_5$, if it is other than hydrogen, may be in the 3 and/or 5 position relative to the carbon of the ring bearing the nitrogen substituted with the radicals $R_1$ and $R_2$, for example in the 3 position relative to that carbon.

In certain embodiments, the radicals $R_5$, which may be identical or different, are chosen from hydrogen atoms; linear or branched $C_1$–$C_4$ alkyl radicals; —O—$R_{51}$ where $R_{51}$ is a linear $C_1$–$C_4$ alkyl radical; —$R_{52}$—O—$CH_3$ where $R_{52}$ is a linear $C_2$–$C_3$ alkyl radical; and —$R_{53}$—N$(R_{54})_2$ where $R_{53}$ is a linear $C_2$–$C_3$ alkyl radical and $R_{54}$, which may be identical or different, is chosen from hydrogen atoms and methyl radicals.

For example, $R_5$, which may be identical or different, may be chosen from hydrogen atoms, methyl radicals, and methoxy radicals, and $R_5$, for example, may be a hydrogen atom.

According to one embodiment, the radicals $R_6$, which may be identical or different, are chosen from hydrogen atoms; linear or branched $C_1$–$C_4$ alkyl radicals; —X wherein X is chosen from chlorine, bromine, and fluorine atoms; —$R_{61}$—O—$R_{62}$ wherein $R_{61}$ is a linear $C_2$–$C_3$ alkyl radical and $R_{62}$ is a methyl radical; —$R_{63}$—N$(R_{64})_2$ wherein $R_{63}$ is a linear $C_2$–$C_3$ alkyl radical and $R_{64}$, which may be identical or different, is chosen from hydrogen atoms and methyl radicals; —N$(R_{65})_2$ in which $R_{65}$, which may be identical or different, is chosen from hydrogen atoms and linear $C_2$–$C_3$ alkyl radicals; —NHCO $R_{66}$ wherein $R_{66}$ is chosen from $C_1$–$C_2$ alkyl radicals, $C_1$–$C_2$ chloroalkyl radicals, and the radicals —$R_{67}$—$NH_2$, —$R_{67}$—NH$(CH_3)$, —$R_{67}$—N$(CH_3)_2$, —$R_{67}$—N$^+(CH_3)_3$, and —$R_{67}$—N$^+(CH_2CH_3)_3$ wherein $R_{67}$ is a $C_1$–$C_2$ alkyl radical.

It is pointed out that the substituent $R_6$, if it is other than hydrogen, may be in the 2 and/or 4 position relative to the nitrogen atom of the pyridinium ring, for example in the 4 position relative to that nitrogen atom.

In certain embodiments, these radicals $R_6$, which may be identical or different, are chosen from hydrogen atoms, methyl radicals, and ethyl radicals. $R_6$ for example may be a hydrogen atom.

As regards the radicals $R_3$ and $R_4$, these radicals, which may be identical or different, may be chosen from hydrogen atoms and alkyl radicals comprising 1 to 4 carbon atoms, such as methyl radicals. For example, $R_3$ and $R_4$ may each be a hydrogen atom.

As mentioned above, X is chosen from:
linear or branched alkyl radicals comprising 1 to 14 carbon atoms and alkenyl radicals comprising 2 to 14 carbon atoms, wherein said alkyl radicals and said alkenyl radicals are optionally interrupted with at least one entity chosen from hetero atoms, groups comprising at least one hetero atom, and halogen atoms, and are optionally substituted with at least one entity chosen from hetero atoms, groups comprising at least one hetero atom, and halogen atoms;
5- or 6-membered heterocyclic radicals optionally substituted with at least one entity chosen from
linear or branched alkyl radicals comprising 1 to 14 carbon atoms,
linear or branched aminoalkyl radicals comprising 1 to 4 carbon atoms, optionally substituted with at least one hetero atom; and
halogen atoms;
fused or non-fused, aromatic or diaromatic radicals, optionally separated with at least one alkyl radical comprising 1 to 4 carbon atoms, the aromatic or diaromatic radicals optionally being substituted with at least one entity chosen from halogen atoms and alkyl radicals which comprise 1 to 10 carbon atoms and are optionally substituted with at least one entity chosen from hetero atoms and groups comprising at least one hetero atom and are optionally substituted with at least one entity chosen from hetero atoms and groups comprising at least one hetero atom; and
dicarbonyl radicals.

In addition, the group X may comprise at least one cationic charge.

Thus, X may be chosen from linear or branched alkyl radicals comprising 1 to 14 carbon atoms and alkenyl radicals comprising 2 to 14 carbon atoms, and X may be substituted with at least one entity chosen from oxygen atoms, nitrogen atoms, groups bearing at least one hetero atom, fluorine atoms, and chlorine atoms.

Among the groups of this type that may be mentioned are hydroxyl, alkoxy (for example, having 1–4 carbons), amino, ammonium, amido, carbonyl, and carboxyl groups (e.g., —COO— and —O—CO—), for example an alkyloxy radical.

It should be noted that the nitrogen atom, if it is present, may be in a quaternized or non-quaternized form. In this case, the other radical or the other two radicals borne by the quaternized or non-quaternized nitrogen atom may be identical or different and may be chosen from hydrogen atoms and $C_1$–$C_4$ alkyl radicals, for example methyl radicals.

According to another embodiment, the group X is chosen from 5- or 6-membered heterocyclic radicals of the imidazolo, pyrazolo, triazino, and pyridino types, optionally substituted with at least one entity chosen from linear or branched alkyl radicals comprising 1 to 14 carbon atoms, for example 1 to 10 carbon atoms or for example 1 to 4 carbon atoms; linear or branched aminoalkyl radicals comprising 1 to 10 carbon atoms, for example 1 to 4 carbon atoms, optionally substituted with at least one entity chosen from groups comprising at least one hetero atom (such as hydroxyl radicals) and from halogen atoms. It should be noted that the amino group may be linked to the heterocycle.

In accordance with another embodiment, the group X is chosen from aromatic radicals (such as those comprising 6 carbon atoms) and fused or non-fused diaromatic radicals (such as those comprising 10 to 12 carbon atoms), optionally separated with an alkyl radical comprising 1 to 4 carbon atoms, the aromatic or diaromatic radicals optionally being substituted with at least one entity chosen from halogen atoms and alkyl radicals comprising 1 to 10 carbon atoms, for example 1 to 4 carbon atoms, optionally interrupted with at least one entity chosen from oxygen atoms, nitrogen atoms, and groups comprising at least one hetero atom (for instance carbonyl, carboxyl, amido, amino, and ammonium radicals).

It should be noted that the aromatic radical, for example phenyl radical, is linked to the groups $CR_3R_4$ via bonds in positions 1,2; 1,3; or 1,4, such as in positions 1,3 and 1,4. If the phenyl radical linked via bonds in positions 1,4 comprises one or two substituents, this or these substituents may be located in position 1,4 relative to one of the groups $CR_3R_4$. If the phenyl radical linked via bonds in positions 1,3 comprises one or two substituents, this or those substituents may be located in position 1 and/or 3 relative to one of the groups $CR_3R_4$.

In the case where the radical is diaromatic, it may be non-fused and may comprise two phenyl radicals optionally separated with at least one of a single bond (i.e., a carbon of each of the two rings) and an alkyl radical, for example $CH_2$ and $C(CH_3)_2$ radicals. In certain embodiments, the aromatic radicals do not comprise a substituent. It should be noted that the diaromatic radical is linked to the groups $CR_3R_4$ via bonds in positions 4,4'.

As examples of groups X that are suitable, mention may be made of linear or branched alkyl radicals comprising 1 to 13 carbon atoms, such as methylene, ethylene, propylene, isopropylene, n-butylene, pentylene, and hexylene; 2-hydroxypropylene; 2-hydroxy-n-butylene; $C_1$–$C_{13}$ alkylene radicals substituted or interrupted with at least one entity chosen from nitrogen atoms, oxygen atoms, and groups comprising at least one hetero atom (hydroxyl, amino, ammonium, carbonyl, and carboxyl groups, for example), such as —$CH_2CH_2OCH_2CH_2$—, 1,6-dideoxy-d-mannitol, —$CH_2N^+(CH_3)_2CH_2$—, —$CH_2CH_2N^+(CH_3)_2$—$(CH_2)_6N^+(CH_3)_2$—$CH_2CH_2$—, CO—CO—, 3,3-dimethylpentylene, 2-acetoxyethylene, butylene-1,2,3,4-tetraol; —CH=CH—; aromatic or diaromatic radicals substituted with at least one entity chosen from alkyl radicals, groups comprising at least one hetero atom, and halogen atoms, such as 1,4-phenylene, 1,3-phenylene, 1,2-phenylene, 2,6-fluorobenzene, 4,4'-biphenylene, 1,3-(5-methylbenzene), 1,2-bis(2-methoxy)benzene, bis(4-phenyl)methane, methyl 3,4-benzoate, and 1,4-bis(amidomethyl)phenyl; and heterocyclic radicals such as pyridine, and derivatives thereof such as 2,6-bispyridine, imidazole, imidazolium, and triazine.

According to another embodiment disclosed herein, X is chosen from linear or branched $C_1$–$C_{13}$ alkyl radicals; —$CH_2CH(OH)CH_2$—; —$CH_2CH(Cl)CH_2$—; —$CH_2CH_2$—$OCOCH_2$—; —$CH_2CH_2COOCH_2$—; —Ra—O—Rb— wherein Ra is a linear $C_2$–$C_6$ alkyl radical and Rb is a linear $C_1$–$C_2$ alkyl radical; -Rc-N(Rd)-Re— wherein Rc is a $C_2$–$C_9$ alkyl radical, Rd is chosen from hydrogen atoms and $C_1$–$C_2$ alkyl radicals, and Re is a $C_1$–$C_6$ alkyl radical; -Rf-$N^+(Rg)_2$-Rh— wherein Rf is a linear $C_2$–$C_9$ alkyl radical, Rg, which may be identical, are chosen from $C_1$–$C_2$ alkyl radicals, and Rh is a linear $C_1$–$C_6$ alkyl radical; and —CO—CO—.

X may furthermore represent an imidazole radical, optionally substituted with at least one alkyl radical comprising 1 to 14 carbon atoms, for example 1 to 10 carbon atoms or for example 1 to 4 carbon atoms, for instance the divalent radicals having the following formula:

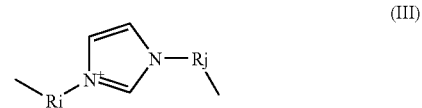

(III)

in which Ri and Rj, which may be identical or different, are chosen from linear $C_1$–$C_6$ alkyl radicals;

X may similarly be chosen from the divalent triazine-based radicals below:

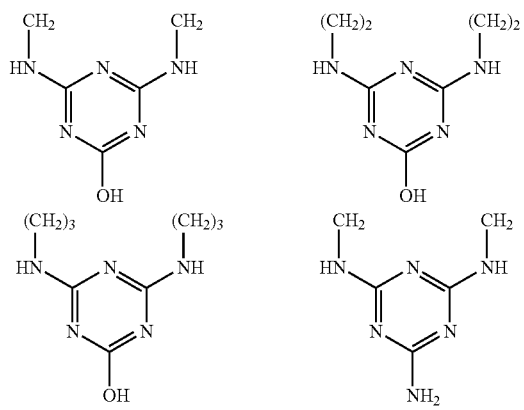

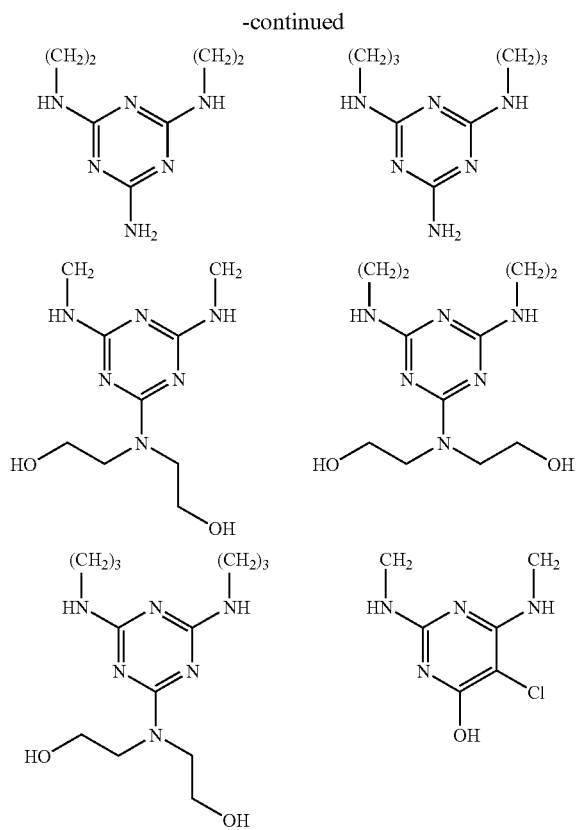

According to another embodiment, X may represent the divalent aromatic radicals below:

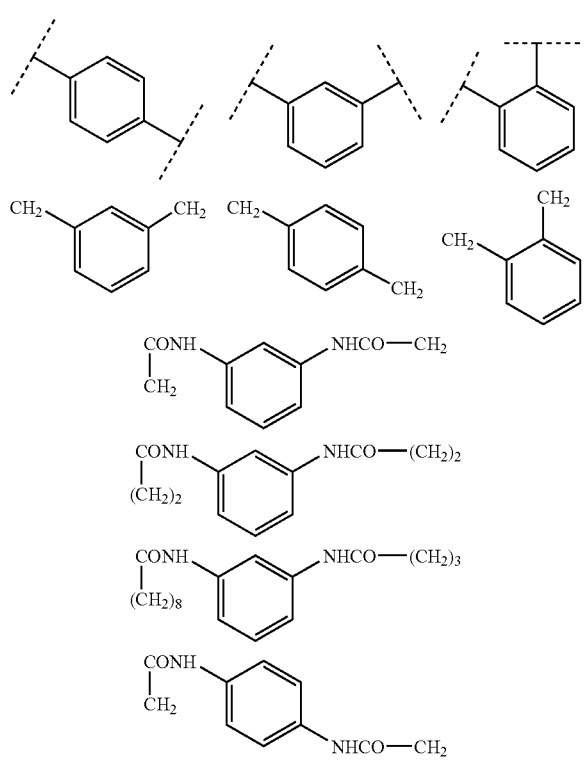

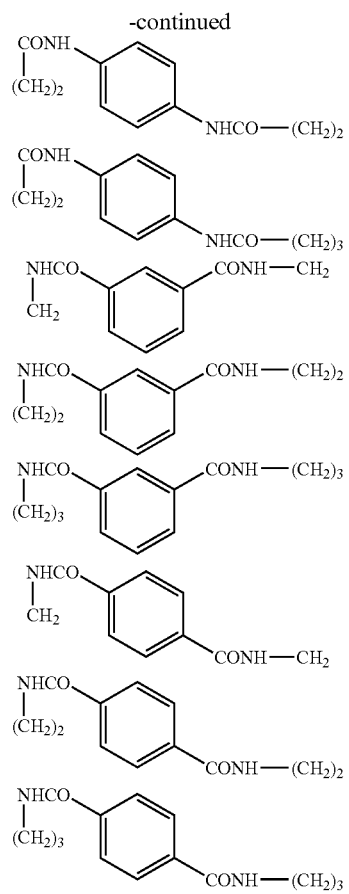

In the general formula of these fluorescent compounds, $Y^-$ is chosen from organic and mineral anions. If there are several anions $Y^-$, these anions may be identical or different.

Among the anions of mineral origin that may be mentioned, without wishing to be limited thereto, are anions derived from halogen atoms, such as chlorides and iodides; sulphates; bisulphates; nitrates; phosphates; hydrogen phosphates; dihydrogen phosphates; carbonates; and bicarbonates.

Among the anions of organic origin that may be mentioned are anions derived from the salts of saturated or unsaturated, aromatic or non-aromatic monocarboxylic or polycarboxylic, sulphonic and sulphuric acids, optionally substituted with at least one entity chosen from hydroxyl radicals, amino radicals, and halogen atoms. Non-limiting examples that are suitable for use include acetates, hydroxyacetates, aminoacetates, (tri)chloro-acetates, benzoxyacetates, propionates and derivatives comprising a chlorine atom, fumarates, oxalates, acrylates, malonates, succinates, lactates, tartrates, glycolates, citrates, benzoates and derivatives comprising at least one radical chosen from methyl radicals and amino radicals, alkyl sulphates, tosylates, benzenesulphonates, and toluene-sulphonates.

In certain embodiments, the anions Y, which may be identical or different, may be chosen from chloride, sulphate, methosulphate, and ethosulphate.

Finally, the integer n is at least equal to 2 and at most equal to the number of cationic charges present in the at least one fluorescent dye compound.

In certain embodiments, the fluorescent dye compounds that have just been described in detail are symmetrical compounds.

These compounds may be synthesized by reacting α-picoline with a reagent comprising two leaving groups that may be chosen from halogen atoms, such as bromine and chlorine, tolylsulphonyl groups, and methanesulphonyl groups.

This reaction may take place in the presence of a solvent, for instance dimethylformamide.

The number of moles of α-picoline is generally in the region of 2 per mole of reagent comprising the leaving groups.

In addition, the reaction is usually performed at the reflux temperature of the reagent and/or of the solvent if a solvent is present.

The product derived from this reaction is then placed in contact with a corresponding aldehyde having the following formula:

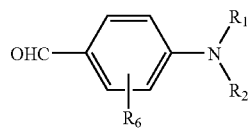

in which $R_1$, $R_2$ and $R_6$ have the same meanings as indicated above.

In this case also, the reaction may be performed in the presence of a suitable solvent, which is, for example, at reflux.

It should be noted that the radicals $R_1$ and $R_2$ of the aldehyde may have the meaning indicated in the general formula detailed previously.

It is also possible to use an aldehyde for which the radicals represent hydrogen atoms and to perform, in accordance with standard methods, the substitution of these hydrogen atoms with suitable radicals as described in the general formula once the second step is complete.

Reference may be made for example to syntheses as described in U.S. Pat. No. 4,256,458.

The at least one fluorescent dye present in the composition disclosed herein may be present in an amount ranging from 0.01% to 20% by weight, such as from 0.05% to 10% by weight, or such as from 0.1% to 5% by weight, relative to the total weight of the composition.

The composition also comprises at least one compound comprising an acid functional group.

More specifically, the at least one compound comprising an acid functional group is chosen from those with a molecular weight of less than 500 g/mol, and chosen from mineral compounds and organic compounds comprising at least one entity chosen from carboxylic functional groups, sulphonic functional groups, linear or branched, saturated or unsaturated hydrocarbon-based radicals comprising 1 to 30 carbon atoms, and aromatic radicals comprising 6 to 30 carbon atoms, the hydrocarbon-based radicals optionally being substituted with at least one entity chosen from hetero atoms, groups comprising at least one hetero atom, and halogen atoms, and optionally being interrupted with at least one entity chosen from hetero atoms and groups comprising at least one hetero atom.

As regards the mineral compounds, mention may be made of strong acids such as hydrochloric acid, sulphuric acid, orthophosphoric acid, and mixtures thereof.

As regards the organic acid compound, this compound may be chosen from compounds comprising at least one entity chosen from carboxylic functional groups, sulphonic functional groups, saturated or unsaturated, linear or branched hydrocarbon-based radicals comprising 1 to 30 carbon atoms, and aromatic radicals comprising 6 to 30 carbon atoms, the hydrocarbon-based radicals optionally being substituted with at least one group chosen from —OH, —$NH_2$, NHR, and —OR, wherein R is chosen from $C_1$–$C_4$ alkyl radicals and halogen atom, for instance chlorine and fluorine, and mixtures thereof. In certain embodiments, the organic acid compound is chosen from compounds comprising at least one entity chosen from carboxylic functional groups, aromatic radicals comprising 6 to 30 carbon atoms; and sulphonic functional group, the hydrocarbon radicals being optionally substituted and interrupted as indicated above.

As examples of suitable organic compounds, mention may be made of monocarboxylic acids, for instance acetic acid, lactic acid, tartaric acid, benzoic acid and anisidic acid, for example benzoic and anisidic acid; natural and synthetic amino acids, in their L, D, or racemic form, such as taurine, lysine, arginine, and aspartic acid; and polyacids, for instance citric acid, succinic acid, maleic acid, and adipic acid, for example, succinic acid, maleic acid and adipic acid; and mixtures thereof.

The at least one compound comprising an acid functional group may be present in an amount ranging from 0.001% to 25% by weight relative to the weight of the composition, for example from 0.01% to 10% by weight relative to the weight of the composition.

It should be noted that the pH of the composition may range from 3 to 12, for example from 5 to 11.

If necessary, the pH of the composition may be controlled by adding a basifying agent chosen, for example, from aqueous ammonia, alkaline carbonates, alkanolamines such as monoethanolamine, diethanolamin, triethanolamine and derivatives thereof, sodium hydroxide, potassium hydroxide, and the compounds of formula (E) below:

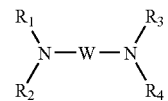

in which W is a propylene residue optionally substituted with an entity chosen from hydroxyl groups and $C_1$–$C_6$ alkyl radicals; $R_1$, $R_2$, $R_3$ and $R_4$, which may be identical or different, are chosen from hydrogen atoms, $C_1$–$C_6$ alkyl radicals, and $C_1$–$C_6$ hydroxyalkyl radicals.

The cosmetically acceptable medium may comprise water or a mixture of water and at least one common organic solvent.

Among the solvents that are suitable for use, mention may be made of alcohols such as ethyl alcohol, isopropyl alcohol, benzyl alcohol, and phenylethyl alcohol; glycols; glycol ethers, for instance ethylene glycol monomethyl ether; monoethyl ether; monobutyl ether; propylene glycol and ethers thereof, for instance propylene glycol monomethyl ether; butylene glycol; dipropylene glycol; diethylene glycol alkyl ethers, for instance diethylene glycol monoethyl ether; monobutyl ether; and polyols, for instance glycerol. Polyethylene glycols, polypropylene glycols, and mixtures of all these compounds may also be used as solvent.

The common solvents described above may be present in an amount ranging from 1% to 40% by weight, for example from 5% to 30% by weight relative to the total weight of the composition.

According to one embodiment disclosed herein, the composition may comprise, in addition to the at least one fluorescent dye, at least one additional non-fluorescent direct dyes chosen from nonionic, cationic, and anionic direct dyes, for example, nitrobenzene dyes.

The following red and orange nitrobenzene direct dyes may be suitable for use:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

The compositions disclosed herein may also comprise, in addition to or instead of these nitrobenzene dyes, at least one additional direct dye chosen from yellow, green-yellow, blue, and violet nitrobenzene dyes, azo dyes, anthraquinone dyes, naphthoquinone dyes, benzoquinone dyes, phenothiazine dyes, indigoid dyes, xanthene dyes, phenanthridine dyes, phthalocyanin dyes, triarylmethane-based dyes, and mixtures thereof.

These additional direct dyes may be basic dyes, among which mention may be made of the dyes known in the Colour Index, 3rd edition, under the names "Basic Brown 16", "Basic Brown 17", "Basic Yellow 57", "Basic Red 76", "Basic Violet 10", "Basic Blue 26", and "Basic Blue 99". Mention may also be made of acidic direct dyes, among which mention may be made of the dyes known in the Colour Index, 3rd edition, under the names "Acid Orange 7", "Acid Orange 24", "Acid Yellow 36", Acid Red 33", "Acid Red 184", "Acid Black 2", "Acid Violet 43", and "Acid Blue 62", and cationic direct dyes such as those described in Patent Application Nos. WO 95/01772, WO 95/15144, and EP-A-0 714 954, the contents of which are incorporated by reference herein.

Among the additional yellow and green-yellow nitrobenzene direct dyes that may be mentioned, for example, are the compounds chosen from:
1-1-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulphonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-n itrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Among the additional blue and violet nitrobenzene direct dyes that may be mentioned, for example, are the compounds chosen from:
1-(β-hydroxyethyl)amino-4-N,N-bis(β-hydroxyethyl)amino-2-nitrobenzene,
1-(γ-hydroxypropyl)amino-4, N,N-bis(β-hydroxyethyl)amino-2-nitrobenzene,
1-(β-hydroxyethyl)amino-4-(N-methyl-N-β-hydroxyethyl)amino-2-nitrobenzene,
1-(1-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene,
2-nitroparaphenylenediamines having the following formula:

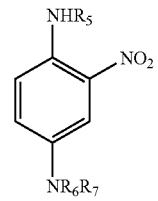

in which:
$R_6$ is chosen from $C_1$–$C_4$ alkyl radicals, β-hydroxyethyl radicals, β-hydroxypropyl radicals, and γ-hydroxypropyl radicals; and
$R_5$ and $R_7$, which may be identical or different, are chosen from β-hydroxyethyl radicals, β-hydroxypropyl radicals, γ-hydroxypropyl radicals, and β,γ-dihydroxypropyl radicals, at least one of the radicals $R_6$, $R_7$, and $R_5$ being a γ-hydroxypropyl radical and $R_6$ and $R_7$ not simultaneously being a β-hydroxyethyl radical when $R_s$ is a γ-hydroxypropyl radical, such as those compounds described in French Patent No. FR 2 692 572.

When present, the at least one additional direct dye may be present in an amount randing from 0.0005% to 12% by weight relative to the total weight of the composition, for example from 0.005% to 6% by weight relative to the total weight of the composition.

When intended for oxidation dyeing, the compositions disclosed herein may comprise, in addition to the at least one fluorescent dye compound, at least one oxidation base chosen from the oxidation bases conventionally used for oxidation dyeing and among which mention may be made of para-phenylenediamines, bis(phenyl)alkylenediamines, para-aminophenols, ortho-aminophenols, heterocyclic bases, and the acid and alkaline addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4'-aminophenyl-1-(3-hydroxy)pyrrolidine, and the acid and alkaline addition salts thereof.

Among the para-phenylenediamines mentioned above, mention may be made of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid and alkaline addition salts thereof.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,5-dioxaoctane, and the acid and alkaline addition salts thereof.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the acid and alkaline addition salts thereof.

Among the ortho-aminophenols that may be mentioned, for example, are 2-aminophenol, 2-amino-5-methylphenol, 2-amino-6-methylphenol, 5-acetamido-2-aminophenol, and the acid and alkaline addition salts thereof.

Among the heterocyclic bases that may be mentioned, for example, are pyridine derivatives, pyrimidine derivatives, pyrazole derivatives, and the acid and alkaline addition salts thereof.

When present, the at least one oxidation base may be present in an amount ranging from 0.0005% to 12% by weight relative to the total weight of the composition, for example from 0.005% to 6% by weight relative to this weight.

When they are intended for oxidation dyeing, the compositions in accordance with certain embodiments may also comprise, in addition to the at least one fluorescent dye and the at least one oxidation base, at least one coupler so as to modify or to enrich with glints the shades obtained using the at least one fluorescent dye and the at least one oxidation base.

The couplers that may be used in the composition in accordance with certain embodiments may be chosen from the couplers conventionally used in oxidation dyeing, and among which mention may be made of meta-phenylenediamines, meta-aminophenols, meta-diphenols, heterocyclic couplers, and the acid and alkaline addition salts thereof.

These couplers may, for example, be chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1;3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-di-hydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo[1,5-a]benzimidazole, and the acid and alkaline addition salts thereof.

When present, the at least one coupler may be present in an amount ranging from 0.0001% to 10% by weight, for example from 0.005% to 5% by weight relative to the total weight of the composition.

In general, the acid addition salts that may be used according to certain embodiments (oxidation bases and couplers) may be chosen from the hydrochlorides, hydrobromides, sulphates, citrates, succinates, tartrates, tosylates, benzenesulphonates, lactates, and acetates.

The alkaline addition salts that may be used according to certain embodiments (oxidation bases and couplers) may be chosen from addition salts with alkali metals, alkaline-earth metals, ammonia, organic amines, including alkanolamines, and the compounds of formula (E).

The compositions disclosed herein may also comprise various conventionally used adjuvants, such as anionic, cationic, nonionic, amphoteric, and zwitterionic surfactants, and mixtures thereof; anionic, cationic, nonionic, amphoteric, and zwitterionic polymers other than those disclosed herein, and mixtures thereof; mineral thickeners; antioxidants; penetrating agents; sequestering agents; fragrances; dispersants; conditioners, for instance cations; modified or unmodified, volatile or non-volatile silicones; film-forming agents; ceramides; preserving agents; stabilizers; and opacifiers.

Among the thickeners that may be mentioned are thickening systems based on associative polymers that are well-known to those skilled in the art, such as nonionic, anionic, cationic, and amphoteric associative polymers.

When at least one surfactant, such as nonionic, anionic, and amphoteric surfactants, are present, the at least one surfactant may be present in an amount ranging from 0.01% to 30% by weight relative to the weight of the composition.

Needless to say, a person skilled in the art will take care to select this or these optional additional compounds such that the advantageous properties intrinsically associated with the compositions disclosed herein are not, or are not substantially, adversely affected by the envisaged addition(s).

The compositions according to certain embodiments may be in various forms, such as in the form of liquids, shampoos, creams, gels, and any other suitable form.

One form that may be mentioned is the form of a lightening dye shampoo comprising, in a cosmetically acceptable aqueous medium, the composition disclosed herein.

In the composition disclosed herein, when at least one oxidation base is used, optionally in the presence of at least one coupler, or when the at least one fluorescent dye is used in the context of a lightening direct dyeing, then the composition in accordance with one embodiment may also comprise at least one oxidizing agent.

The at least one oxidizing agent may be chosen, for example, from hydrogen peroxide, urea peroxide, alkali metal bromates, persalts such as perborates and persulphates, and enzymes such as peroxidases, two-electron oxidoreductases, and four-electron oxidoreductases. The use of hydrogen peroxide and enzymes, for example, may be mentioned.

Another embodiment is also the method of using, for dyeing human keratin materials with a lightening effect, a composition comprising, in a cosmetically acceptable medium, at least one fluorescent dye that is soluble in the medium and at least one compound comprising an acid functional group, with a molecular weight of less than 500 g/mol, chosen from mineral compounds and organic compounds comprising at least one entity chosen from carboxylic functional groups, sulphonic functional groups, linear or branched, saturated or unsaturated hydrocarbon-based radicals comprising 1 to 30 carbon atoms, and aromatic radicals comprising 6 to 30 carbon atoms, the hydrocarbon-based radicals optionally being substituted with at least one entity chosen from hetero atoms, groups comprising at least one hetero atom, and halogen atoms, and being optionally interrupted with at least one entity chosen from hetero atoms and groups comprising at least one hetero atom.

In the context of this use, the at least one fluorescent dye compound may be chosen from fluorescent compounds belonging to the following families: naphthalimides; cationic coumarins; non-cationic coumarins; xanthenodiquinolizines (such as sulphorhodamines); azaxanthenes; naphtholactams; azlactones; oxazines; thiazines; dioxazines; monocationic or polycationic fluorescent dyes chosen from azo, azomethine, and methine flourescent dyes; and mixtures thereof.

Additional compounds that may be mentioned include the compounds of formulae F1, F2, and F3 already detailed previously.

It is likewise possible to use the compounds of structure (F4) below:

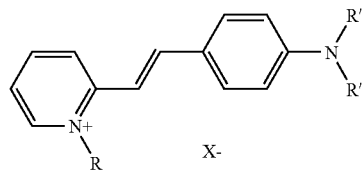

in which formula R is chosen from methyl and ethyl radicals; R' is a methyl radical, X— is an anion such as chloride, iodide, sulphate, methosulphate, acetate, and perchlorate. An example of a compound of this type that may be mentioned is the Photosensitizing Dye NK-557 sold by the company Ubichem, for which R is an ethyl radical, R' is a methyl radical, and X— is an iodide.

In one embodiment, the at least one fluorescent dye compound is not 2-[2-(4-dialkylamino)phenylethenyl]-1-alkyl pyridinium in which the alkyl radical of the pyridinium nucleus is chosen from methyl and ethyl radicals and that of the benzene nucleus represents a methyl radical, and in which the counterion is a halide.

Everything that has been described hereinabove regarding the nature and contents of the various additives present in the compositions disclosed herein remains valid and will not be repeated in this section.

As used herein, the term "human keratin materials" means the skin, the hair, the nails, the eyelashes and the eyebrows, for example dark skin and artificially colored and/or pigmented hair.

As used herein, the term "dark skin" means a skin whose lightness L* measured in the CIEL L*a*b* system is less than or equal to 45, for example less than or equal to 40, given that L*=0 is equivalent to black and L*=100 is equivalent to white. The skin types corresponding to this lightness may be African skin, Afro-American skin, Hispano-American skin, Indian skin, and North African skin.

As used herein, the expression "artificially dyed and/or pigmented hair" means hair whose tone height is less than or equal to 6 (e.g., dark blond), for example less than or equal to 4 (e.g., chestnut-brown).

The lightening of the hair is evaluated by the "tone height", which characterizes the degree or level of lightening. The notion of "tone" is based on the classification of the natural shades, one tone separating each shade from the shade immediately following or preceding it. This definition and the classification of the natural shades are well-known to hairstyling professionals and are published in the book "Sciences des traitements capillaires [Hair treatment sciences]" by Charles Zviak, 1988, published by Masson, pp. 215 and 278.

The tone heights range from 1 (black) to 10 (light blond), one unit corresponding to one tone. The higher the figure, the lighter the shade.

Another embodiment thus concerns a process for dyeing human keratin fibers with a lightening effect, comprising:
a) applying the composition disclosed herein to the keratin fibers, for a time that is sufficient to develop a desired coloration and lightening,
b) optionally rinsing the fibers,
c) optionally washing the fibers with shampoo and optionally rinsing the fibers,
d) drying the fibers or leaving the fibers to dry.

Another embodiment is also a process for coloring dark skin with a lightening effect, comprising applying the composition that has just been described to the skin, and then drying the skin or leaving the skin to dry. In one embodiment, this composition does not comprise any oxidation base or coupler and is not used in the presence of an oxidizing agent.

Everything that has been described previously regarding the various constituent components of the compositions disclosed herein remains valid, and reference may be made thereto.

For example, the processes disclosed herein are suitable for treating human keratin fibers, such as artificially colored and/or pigmented hair, and alternatively dark skin.

In another example, the fibers that may be treated with the process disclosed herein have a tone height of less than or equal to 6 (e.g., dark blond), such as less than or equal to 4 (e.g., chestnut-brown).

Furthermore, a dark skin capable of being treated in accordance with certain embodiments has a lightness L*, measured in the CIEL L*a*b* system, of less than or equal to 45, such as less than or equal to 40.

According to one embodiment disclosed herein, the process of dyeing fibers with a lightening effect is performed with a composition that does not comprise any oxidation dyes or coupler and in the absence of an oxidizing agent.

According to another embodiment disclosed herein the process of dyeing fibers with a lightening effect is performed with a composition that does not comprise any oxidation dyes or coupler, but in the presence of at least one oxidizing agent.

According to one embodiment of these dyeing processes, at least one composition as defined above is applied to the fibers, such as the hair, for a time that is sufficient to develop the desired coloration and lightening, after which the fibers are rinsed, optionally washed with shampoo, rinsed again and dried.

According to another embodiment of these dyeing processes, at least one composition as defined above is applied to the fibers, such as the hair, without final rinsing.

Yet another embodiment of these dyeing processes, comprises separately storing, on the one hand, a composition as disclosed herein optionally comprising at least one oxidation base and optionally comprising at least one coupler, and, on the other hand, a composition comprising, in a cosmetically acceptable medium, at least one oxidizing agent, and mixing them together at the time of use, after which applying this mixture to the keratin fibers, such as the hair, for a time that is sufficient to develop the desired coloration, and rinsing the fibers, optionally washing the fibers with shampoo, rinsing the fibers again and drying the fibers.

The time required to develop the coloration and to obtain the lightening effect on the fibers, especially the hair, is 5 to 60 minutes, for example 5 to 40 minutes.

The temperature required to develop the coloration and to obtain the lightening effect may range from room temperature (15° C. to 25° C.) to 80° C., for example from 15° C. to 40° C.

Another embodiment is a multi-compartment device for dyeing keratin fibers, such as the hair, with a lightening effect, comprising at least one compartment comprising a composition as disclosed herein, and at least one other compartment comprising a composition comprising at least one oxidizing agent. This device may be equipped with a means for applying the desired mixture to the fibers, such as the devices described in French Patent No. FR 2 586 913.

It should be noted that the composition disclosed herein, if it is used to treat keratin fibers, for example chestnut-brown hair, makes it possible to achieve the following results:

If the reflectance of the hair is measured when it is irradiated with visible light in the wavelength range from 400 to 700 nanometers, and if the curves of reflectance as a function of the wavelength are compared for hair treated with the composition disclosed herein and untreated hair, it is found that the reflectance curve corresponding to the treated hair, in a wavelength range from 500 to 700 nanometers, is higher than that corresponding to the untreated hair.

This means that, in the wavelength range from 500 to 700 nanometers, for example from 540 to 700 nanometers, there is at least one range in which the reflectance curve corresponding to the treated hair is higher than the reflectance curve corresponding to the untreated hair. As used herein, the term "higher than" means a difference of at least 0.05%, for example at least 0.1% of reflectance.

However, it is pointed out that there may be, within the wavelength range from 500 to 700 nanometers, for example from 540 to 700 nanometers, at least one range in which the reflectance curve corresponding to the treated fibers is either superimposable on or lower than the reflectance curve corresponding to the untreated fibers.

In one embodiment, the wavelength at which the difference is maximal between the reflectance curve for the treated hair and that for the untreated hair is in the wavelength range from 500 to 650 nanometers, for example the wavelength range from 550 to 620 nanometers.

In addition, the compositions disclosed herein may be capable of lightening the hair and the skin in a shade which, measured in the CIEL L*a*b* system, has a variable b* of greater than or equal to 6, with a b*/absolute value of a* ratio of greater than 1.2 according to the selection test described below.

Selection Test

The composition is applied to chestnut-brown keratin fibers, i.e., the hair, at a rate of 10 grams of composition per 1 gram of chestnut-brown fibers. The composition is spread on so as to cover all of the fibers. The composition is left to act for 20 minutes at room temperature (20° C. to 25° C.). The fibers are then rinsed with water and then washed with a lauryl ether sulphate-based shampoo. The fibers are then dried. The spectrocolorimetric characteristics of the fibers are then measured in order to determine the L*a*b* coordinates.

In the CIEL L*a*b* system, a* and b* indicate two color axes: a* indicates the green/red color axis (+a* is red, -a* is green) and b* indicates the blue/yellow color axis (+b* is yellow and -b* is blue); values close to zero for a* and b* correspond to grey shades.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific examples are reported as precisely as possible. Any numerical values, however, inherently contains certain errors necessarily resulting from the standard deviation found in their respective testing measurements. The following examples are intended to illustrate the invention without limiting the scope as a result.

EXAMPLES

Fluorescent Compound

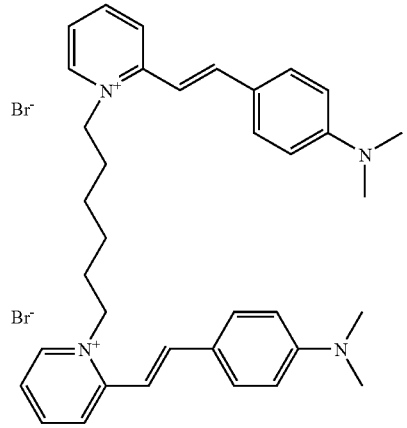

93 g of 2-picoline were reacted with 120 g of 1,6-dibromohexane in dimethylformamide at 110° C. for 5 hours.

The precipitated product was recovered and filtered off.

109 g of the product obtained above were dissolved in methanol and 82.82 g of p-dimethylaminobenzaldehyde were added in two portions, in the presence of pyrrolidine. The mixture was then left for 30 minutes.

The product was recovered in precipitated form.

Analysis by mass spectroscopy: 266.

Elemental analysis: C: 62.43%; H: 6.40%; Br: 23.07%; N: 8.09%.

The formula was as follows: $C_{36}H_{44}N_4.2Br$.

Compositions (Percentages Expressed by Weight of Active Material)

| Composition | 1 | 2 | 3 |
|---|---|---|---|
| Fluorescent compound | 0.6% | 0.6% | 0.6% |
| Compound comprising an acid functional group: | | | |
| Taurine | 0.15% | — | — |
| Succinic acid | — | 0.15% | — |
| Orthophosphoric acid | — | — | 0.15% |
| Distilled water | | qs 100% | |

Each composition was applied to a lock of chestnut-brown hair of tone height 4 with a leave-in time of 20 minutes, a final rinsing operation and a drying operation under a hood for 30 minutes.

Locks of hair with a marked lightening effect were obtained.

What is claimed is:

1. A composition comprising, in a cosmetically acceptable medium,
    at least one fluorescent dye that is soluble in said medium chosen from the following formulae:

(F1)

(F3)

in which:
  $R_1$ and $R_2$, which may be identical or different, are chosen from:
    hydrogen atoms:
    linear or branched alkyl radicals comprising 1 to 10 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;
  aryl and arylalkyl radicals, the aryl radicals comprising 6 carbon atoms and the alkyl groups comprising 1 to 4 carbon atoms; the aryl groups optionally being substituted with at least one linear or branched alkyl radical comprising 1 to 4 carbon atoms, wherein said at least one alkyl radical is optionally interrupted with at least one entity chosen from hetero atoms and groups comprising at least one hetero atom and is optionally substituted with at least one entity chosen from hetero atoms, groups comprising at least one hetero atom, and halogen atoms;
  $R_1$ and $R_2$ may optionally be linked so as to form a heterocycle with the nitrogen atom to which they are attached and may comprise at least one other hetero atom, the heterocycle optionally being substituted with at least one linear or branched alkyl radical, wherein the at least one alkyl radical is optionally interrupted with at least one entity chosen from hetero atoms and groups comprising at least one hetero atom and is optionally substituted with at least one entity chosen from hetero atoms, groups comprising at least one hetero atom, and halogen atoms;
  $R_1$ or $R_2$ may optionally form a heterocycle comprising the nitrogen atom to which they are attached and one of the carbon atoms of the phenyl group comprising the nitrogen atom;
  $R_3$ and $R_4$, which may be identical or different, are chosen from hydrogen atoms and alkyl radicals comprising 1 to 4 carbon atoms;
  $R_5$, which may be identical or different, are chosen from hydrogen atoms, halogen atoms, and linear or branched alkyl radicals comprising 1 to 4 carbon atoms, optionally interrupted with at least one hetero atom;
  $R_6$, which may be identical or different, is chosen from hydrogen atoms; halogen atoms;
    linear or branched alkyl radicals comprising 1 to 4 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;
  X is chosen from;
    linear or branched alkyl radicals comprising 1 to 14 carbon atoms and alkenyl radicals comprising 2 to 14 carbon atoms, wherein said alkyl radicals and said alkenyl radicals are optionally interrupted with at least one entity chosen from hetero atoms and groups comprising at least one hetero atom and are optionally substituted with at least one entity chosen from hetero atoms, groups comprising at least one hetero atom, and halogen atoms;
    5- or 6-membered heterocyclic radicals optionally substituted with at least one entity chosen from
      linear or branched alkyl radicals comprising 1 to 14 carbon atoms, optionally substituted with at least one hetero atom;
      linear or branched aminoalkyl radicals comprising 1 to 4 carbon atoms, optionally substituted with at least one hetero atom; and
      halogen atoms;
    fused or non-fused aromatic or diaromatic radicals, optionally separated with at least one alkyl radical comprising 1 to 4 carbon atoms, the aromatic or diaromatic radicals optionally being substituted with at least one entity chosen from halogen atoms and alkyl radicals comprising 1 to 10 carbon atoms, wherein said alkyl radicals comprising 1 to 10 carbon atoms are optionally interrupted with at least one entity chosen from hetero atoms and groups comprising at least one hetero atom and are optionally substituted with at least one entity chosen from hetero atoms and groups comprising at least one hetero atom;

dicarbonyl radicals;

the group X optionally comprising at least one cationic charge;

a is chosen from 0 and 1:

$Y^-$, which may be identical or different, is chosen from organic and mineral anions; and n is an integer at least equal to 2 and at most equal to the number of cationic charges present in the at least one fluorescent dye; and at least one compound comprising an acid functional group, with a molecular weight of less than 500 g/mol, chosen from mineral compounds and organic compounds comprising at least one entity chosen from carboxylic functional groups, sulphonic functional groups, linear or branched, saturated or unsaturated, hydrocarbon-based radicals comprising 1 to 30 carbon atoms, and aromatic radicals comprising 6 to 30 carbon atoms, wherein said hydrocarbon-based radicals are optionally substituted with at least one entity chosen from hetero atoms, groups comprising at least one hetero atom, and halogen atoms, and are optionally interrupted with at least one entity chosen from hetero atoms and groups comprising at least one heteroato.

2. A composition according to claim 1, wherein the at least one fluorescent dye provides a reflectance maximum that is in the wavelength range from 500 to 650 nanometers.

3. A composition according to claim 2, wherein the at least one fluorescent dye provides a reflectance maximum that is in the wavelength range from 550 to 620 nanometers.

4. A composition according to claim 1, wherein $R_1$ and $R_2$, which may be identical or different, are chosen from linear or branched alkyl radicals comprising 1 to 4 carbon atoms.

5. A composition according to claim 1, wherein $R_1$ and $R_2$, which may be identical or different, are linked so as to form a heterocycle with the nitrogen atom and comprise at least one hetero atom, the heterocycle being substituted with at least one linear or branched alkyl radical comprising 1 to 4 carbon atoms.

6. A composition according to claim 1, wherein the at least one fluorescent dye is present in an amount ranging from 0.01% to 20% by weight relative to the total weight of the composition.

7. A composition according to claim 6, wherein the at least one fluorescent dye is present in an amount ranging from 0.05% to 10% by weight relative to the total weight of the composition.

8. A composition according to claim 7, wherein the at least one fluorescent dye is present in an amount ranging from 0.1% to 5% by weight relative to the total weight of the composition.

9. A composition according to claim 1, wherein the mineral compounds are chosen from strong acids.

10. A composition according to claim 9, wherein the strong acids are chosen from hydrochloric acid, sulphuric acid, orthophosphoric acid, and mixtures thereof.

11. A composition according to claim 1, wherein the organic compounds are chosen from compounds comprising at least one entity chosen from carboxylic functional groups, sulphonic functional groups, linear or branched, saturated or unsaturated hydrocarbon-based radicals comprising from 1 to 30 carbon atoms, and aromatic radicals comprising from 6 to 30 carbon atoms, wherein said hydrocarbon-based radicals are optionally interrupted with and optionally substituted with at least one entity chosen from —OH, —NH$_2$, NHR, and —OR, wherein R is chosen from $C_1$-$C_4$ alkyl radicals, halogen atoms, and mixtures thereof.

12. A composition according to claim 11, wherein the halogen atoms are chosen from chlorine and fluorine.

13. A composition according to claim 1, wherein the acid is chosen from monocarboxylic acids, natural amino acids and synthetic amino acids in a form chosen from L, D and racemic forms, and mixtures thereof.

14. A composition according to claim 13, wherein the monocarboxylic acids are chosen from acetic acid, lactic acid, tartaric acid, benzoic acid, and anisidic acid.

15. A composition according to claim 13, wherein the natural and synthetic amino acids are chosen from taurine, lysine, arginine, and aspartic acid.

16. A composition according to claim 13, wherein the acid is chosen from polyacids.

17. A composition according to claim 16, wherein the polyacids are chosen from citric acid, succinic acid, maleic acid, adipic acid, and mixtures thereof.

18. A composition according to claim 1, wherein the compound comprising an acid functional group is present in an amount ranging from 0.001% to 25% by weight relative to the weight of the composition.

19. A composition according to claim 18, wherein the compound comprising an acid functional group is present in an amount ranging from 0.01% to 10% by weight relative to the weight of the composition.

20. A composition according to claim 1, further comprising at least one surfactant chosen from nonionic, anionic, and amphoteric surfactants.

21. A composition according to claim 20, wherein the at least one surfactant is present in an amount ranging from 0.01% to 30% by weight relative to the total weight of the composition.

22. A composition according to claim 1, further comprising at least one additional non-fluorescent direct dye chosen from nonionic, cationic, and anionic direct dyes.

23. A composition according to claim 22, wherein the at least one additional fluorescent direct dye is chosen from nitrobenzene dyes, azo dyes, anthraquinone dyes, naphthoquinone dyes, benzoquinone dyes, phenothiazine dyes, indigoid dyes, xanthene dyes, phenanthridine dyes, phthalocyanin dyes, and triaryl-methane-based dyes.

24. A composition according to claim 22, wherein the at least one additional fluorescent direct dye is present in an amount ranging from 0.0005% to 12% by weight relative to the total weight of the composition.

25. A composition according to claim 24, wherein the at least one additional fluorescent direct dye is present in an amount ranging from 0.005% to 6% by weight relative to the total weight of the composition.

26. A composition according to claim 1, wherein the composition is in the form of a lightening dyeing shampoo.

27. A composition according to claim 1, further comprising at least one oxidation base chosen from para-phenylenediamines, bis(phenyl)alkylenediamines, para-aminophenols, ortho-aminophenols, heterocyclic bases, and the acid and alkaline addition salts thereof.

28. A composition according to claim 27, wherein the at least one oxidation base is present in an amount ranging from 0.0005% to 12% by weight relative to the total weight of the composition.

29. A composition according to claim 28, wherein the at least one oxidation base is present in an amount ranging from 0.005% to 6% by weight relative to the total weight of the composition.

30. A composition according to claim 27, further comprising at least one coupler chosen from meta-phenylenediamines, meta-aminophenols, meta-diphenols, heterocyclic couplers, and the acid and alkaline addition salts thereof.

31. A composition according to claim 30, wherein the at least one coupler is present in an amount ranging from 0.0001% to 10% by weight relative to the total weight of the dye composition.

32. A composition according to claim 31, wherein the at least one coupler is present in an amount ranging from 0.005% to 5% by weight relative to the total weight of the dye composition.

33. A composition according to claim 1, further comprising at least one oxidizing agent.

34. A composition according to claim 33, wherein the at least one oxidizing agent is chosen from hydrogen peroxide, urea peroxide, alkali metal bromates, persalts, and enzymes.

35. A composition according to claim 34, wherein the persalts are chosen from perborates and persulphates.

36. A composition according to claim 34, wherein the enzymes are chosen from peroxidases, two electron oxidoreductases, and four electron oxidoreductases.

37. A composition according to claim 34, wherein the at least one oxidizing agent is hydrogen peroxide.

38. A composition according to claim 1, wherein the at least one fluorescent dye is a dye in the orange range.

39. A process for dyeing human keratin fibers with a lightening effect, comprising:
a) applying to said fibers a dye composition comprising, in a cosmetically acceptable medium,
at least one fluorescent dye that is soluble in said medium chosen from the following formulae:

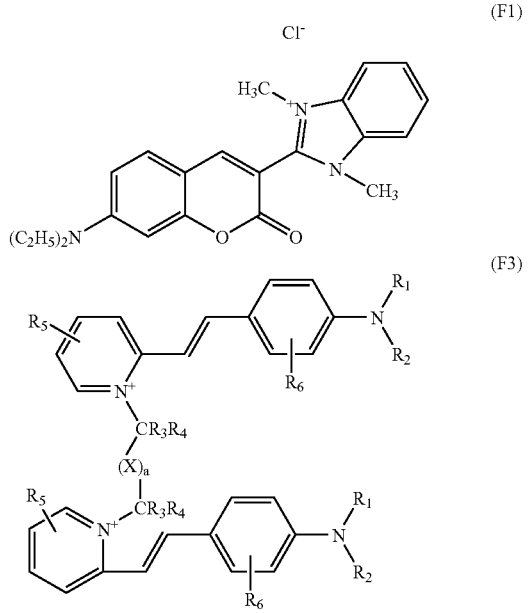

in which:
R$_1$ and R$_2$, which may be identical or different, are chosen from:
hydrogen atoms;
linear or branched alkyl radicals comprising 1 to 10 carbon atoms, optionally interrupted with at least one entity chosen from hetero atoms and
groups comprising at least one hetero atom and optionally substituted with at least one entity chosen from hetero atoms, groups comprising at least one hetero atom, and halogen atoms;
aryl and arylalkyl radicals, the aryl radicals comprising 6 carbon atoms and the alkyl groups comprising 1 to 4 carbon atoms; the aryl groups optionally being substituted with at least one linear or branched alkyl radical comprising 1 to 4 carbon atoms, wherein said at least one alkyl radical is optionally interrupted with at least one entity chosen from hetero atoms and groups comprising at least one hetero atom and is optionally substituted with at least one entity chosen from hetero atoms, groups comprising at least one hetero atom, and halogen atoms;
R$_1$ and R$_2$ may optionally be linked so as to form a heterocycle with the nitrogen atom to which they are attached and may comprise at least one other hetero atom, the heterocycle optionally being substituted with at least one linear or branched alkyl radical, wherein the at least one alkyl radical is optionally interrupted with at least one entity chosen from hetero atoms and groups comprising at least one hetero atom and is optionally substituted with at least one entity chosen from hetero atoms, groups comprising at least one hetero atom, and halogen atoms;
R$_1$ or R$_2$ may optionally form a heterocycle comprising the nitrogen atom to which they are attached and one of the carbon atoms of the phenyl group comprising the nitrogen atom;
R$_3$ and R$_4$, which may be identical or different, are chosen from hydrogen atoms and alkyl radicals comprising 1 to 4 carbon atoms;
R$_5$, which may be identical or different, are chosen from hydrogen atoms, halogen atoms, and linear or branched alkyl radicals comprising 1 to 4 carbon atoms, optionally interrupted with at least one hetero atom;
R$_6$, which may be identical or different, is chosen from hydrogen atoms; halogen atoms;
linear or branched alkyl radicals comprising 1 to 4 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;
X is chosen from:
linear or branched alkyl radicals comprising 1 to 14 carbon atoms and alkenyl radicals comprising 2 to 14 carbon atoms, wherein said alkyl radicals and said alkenyl radicals are optionally interrupted with at least one entity chosen from hetero atoms and groups comprising at least one hetero atom and are optionally substituted with at least one entity chosen from hetero atoms, groups comprising at least one hetero atom, and halogen atoms;

5- or 6-membered heterocyclic radicals optionally substituted with at least one entity chosen from linear or branched alkyl radicals comprising 1 to 14 carbon atoms, optionally substituted with at least one hetero atom;

linear or branched aminoalkyl radicals comprising 1 to 4 carbon atoms, optionally substituted with at least one hetero atom; and halogen atoms;

fused or non-fused aromatic or diaromatic radicals, optionally separated with at least one alkyl radical comprising 1 to 4 carbon atoms, the aromatic or diaromatic radicals optionally being substituted with at least one entity chosen from halogen atoms and alkyl radicals comprising 1 to 10 carbon atoms, wherein said alkyl radicals comprising 1 to 10 carbon atoms are optionally interrupted with at least one entity chosen from hetero atoms and groups comprising at least one hetero atom and are optionally substituted with at least one entity chosen from hetero atoms and groups comprising at least one hetero atom;

dicarbonyl radicals;

the group X optionally comprising at least one cationic charge;

a is chosen from 0 and 1;

$Y^-$, which may be identical or different, is chosen from organic and mineral anions; and n is an integer at least equal to 2 and at most equal to the number of cationic charges present in the at least one fluorescent dye; and at least one compound comprising an acid functional group, with a molecular weight of less than 500 g/mol, chosen from mineral compounds and organic compounds comprising at least one entity chosen from carboxylic functional groups, sulphonic functional groups, linear or branched, saturated or unsaturated, hydrocarbon-based radicals comprising 1 to 30 carbon atoms, and aromatic radicals comprising 6 to 30 carbon atoms, wherein said hydrocarbon-based radicals are optionally substituted with at least one entity chosen from hetero atoms, groups comprising at least one hetero atom, and halogen atoms, and are optionally interrupted with at least one entity chosen from hetero atoms and groups comprising at least one heteroatom;

for a time that is sufficient to develop a desired coloration and lightening, b) optionally rinsing the fibers, and c) optionally washing with fibers with shampoo and optionally rinsing the fibers, and d) drying the fibers or leaving the fibers to dry.

40. A process for dyeing human keratin fibers with a lightening effect, comprising a) separately storing (i) a dye composition comprising, in a cosmetically acceptable medium, at least one fluorescent dye that is soluble in said medium chosen from the following formulae:

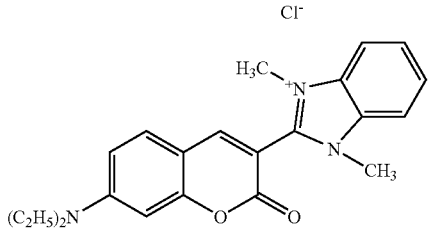

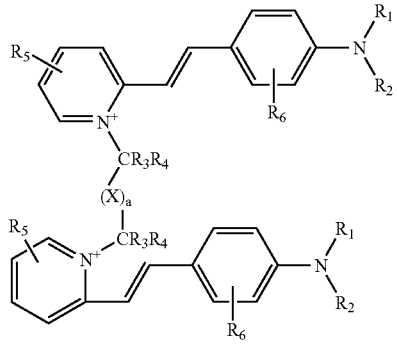

in which:

$R_1$ and $R_2$, which may be identical or different, are chosen from:

hydrogen atoms;

linear or branched alkyl radicals comprising 1 to 10 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;

aryl and arylalkyl radicals, the aryl radicals comprising 6 carbon atoms and the alkyl groups comprising 1 to 4 carbon atoms; the aryl groups optionally being substituted with at least one linear or branched alkyl radical comprising 1 to 4 carbon atoms, wherein said at least one alkyl radical is optionally interrupted with at least one entity chosen from hetero atoms and groups comprising at least one hetero atom and is optionally substituted with at least one entity chosen from hetero atoms, groups comprising at least one hetero atom, and halogen atoms;

$R_1$ and $R_2$ may optionally be linked so as to form a heterocycle with the nitrogen atom to which they are attached and may comprise at least one other hetero atom, the heterocycle optionally being substituted with at least one linear or branched alkyl radical, wherein the at least one alkyl radical is optionally interrupted with at least one entity chosen from hetero atoms and groups comprising at least one hetero atom and is optionally substituted with at least one entity chosen from hetero atoms, groups comprising at least one hetero atom, and halogen atoms;

$R_1$ or $R_2$ may optionally form a heterocycle comprising the nitrogen atom to which they are attached and one of the carbon atoms of the phenyl group comprising the nitrogen atom;

$R_3$ and $R_4$, which may be identical or different, are chosen from hydrogen atoms and alkyl radicals comprising 1 to 4 carbon atoms;

$R_5$, which may be identical or different, are chosen from
hydrogen atoms, halogen atoms, and linear or branched
alkyl radicals comprising 1 to 4 carbon atoms, optionally interrupted with at least one hetero atom;

$R_6$, which may be identical or different, is chosen from
hydrogen atoms; halogen atoms;

linear or branched alkyl radicals comprising 1 to 4 carbon
atoms, optionally interrupted with at least one entity
chosen from hetero atoms and groups comprising at
least one hetero atom and optionally substituted with at
least one entity chosen from hetero atoms, groups
comprising at least one hetero atom, and halogen
atoms;

X is chosen from:
linear or branched alkyl radicals comprising 1 to 14
carbon atoms and alkenyl radicals comprising 2 to 14
carbon atoms, wherein said alkyl radicals and said
alkenyl radicals are optionally interrupted with at
least one entity chosen from hetero atoms and groups
comprising at least one hetero atom and are optionally substituted with at least one entity chosen from
hetero atoms, groups comprising at least one hetero
atom, and halogen atoms;

5- or 6-membered heterocyclic radicals optionally substituted with at least one entity chosen from
linear or branched alkyl radicals comprising 1 to 14
carbon atoms, optionally substituted with at least
one hetero atom;
linear or branched aminoalkyl radicals comprising 1
to 4 carbon atoms, optionally substituted with at
least one hetero atom; and
halogen atoms;
fused or non-fused aromatic or diaromatic radicals,
optionally separated with at least one alkyl radical
comprising 1 to 4 carbon atoms, the aromatic or
diaromatic radicals optionally being substituted with
at least one entity chosen from halogen atoms and
alkyl radicals comprising 1 to 10 carbon atoms,
wherein said alkyl radicals comprising 1 to 10 carbon atoms are optionally interrupted with at least one
entity chosen from hetero atoms and groups comprising at least one hetero atom and are optionally
substituted with at least one entity chosen from
hetero atoms and groups comprising at least one
hetero atom;
dicarbonyl radicals;
the group X optionally comprising at least one cationic
charge;

a is chosen from 0 and 1:
$Y^-$, which may be identical or different, is chosen from
organic and mineral anions; and
n is an integer at least equal to 2 and at most equal to the
number of cationic charges present in the at least one
fluorescent dye; and
at least one compound comprising an acid functional
group, with a molecular weight of less than 500
g/mol, chosen from mineral compounds and organic
compounds comprising at least one entity chosen
from carboxylic functional groups, sulphonic functional groups, linear or branched, saturated or unsaturated, hydrocarbon-based radicals comprising 1 to
30 carbon atoms, and aromatic radicals comprising 6
to 30 carbon atoms, wherein said hydrocarbon-based
radicals are optionally substituted with at least one
entity chosen from hetero atoms, groups comprising
at least one hetero atom, and halogen atoms, and are
optionally interrupted with at least one entity chosen
from hetero atoms and groups comprising at least
one heteroatom;

(ii) a composition comprising, in a cosmetically acceptable medium, at least one oxidizing agent,
b) mixing (i) and (ii) together at the time of use,
c) applying the mixture to the fibers for a time that is
sufficient to develop a desired coloration,
d) optionally rinsing the fibers,
e) optionally washing the fibers with shampoo and optionally rinsing the fibers again, and
f) drying the fibers or leaving the fibers to dry.

41. A process according to claim 39, wherein the composition is applied to hair with a tone height of less than or
equal to 6.

42. A process according to claim 41, wherein the composition is applied to hair with a tone height of less than or
equal to 4.

43. A process according to claim 39, wherein the human
keratin fibers are artificially pigmented and/or dyed.

44. A process for coloring dark skin with a lightening
effect, comprising:
applying to the skin a dye composition comprising, in a
cosmetically acceptable medium,
at least one fluorescent dye that is soluble in said
medium chosen from the following formulae:

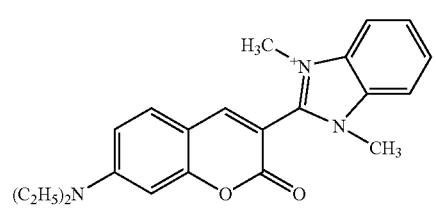

(F1)

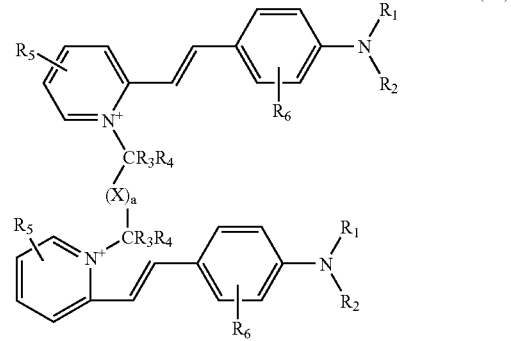

(F3)

in which:
$R_1$ and $R_2$, which may be identical or different, are chosen
from:
hydrogen atoms;
linear or branched alkyl radicals comprising 1 to 10
carbon atoms, optionally interrupted with at least one
entity chosen from hetero atoms and
groups comprising at least one hetero atom and
optionally substituted with at least one entity
chosen from hetero atoms, groups comprising at
least one hetero atom, and halogen atoms;
aryl and arylalkyl radicals, the aryl radicals comprising
6 carbon atoms and the alkyl groups comprising 1 to
4 carbon atoms; the aryl groups optionally being substituted with at least one linear or branched alkyl radical comprising 1 to 4 carbon atoms, wherein said at least one alkyl radical is optionally interrupted with at least one entity chosen from hetero atoms and groups comprising at least one hetero atom and is optionally substituted with at least one entity chosen from hetero atoms, groups comprising at least one hetero atom, and halogen atoms;

$R_1$ and $R_2$ may optionally be linked so as to form a heterocycle with the nitrogen atom to which they are attached and may comprise at least one other hetero atom, the heterocycle optionally being substituted with at least one linear or branched alkyl radical, wherein the at least one alkyl radical is optionally interrupted with at least one entity chosen from hetero atoms and groups comprising at least one hetero atom and is optionally substituted with at least one entity chosen from hetero atoms, groups comprising at least one hetero atom, and halogen atoms;

$R_1$ or $R_2$ may optionally form a heterocycle comprising the nitrogen atom to which they are attached and one of the carbon atoms of the phenyl group comprising the nitrogen atom;

$R_3$ and $R_4$, which may be identical or different, are chosen from hydrogen atoms and alkyl radicals comprising 1 to 4 carbon atoms;

$R_5$, which may be identical or different, are chosen from hydrogen atoms, halogen atoms, and linear or branched alkyl radicals comprising 1 to 4 carbon atoms, optionally interrupted with at least one hetero atom;

$R_6$, which may be identical or different, is chosen from hydrogen atoms; halogen atoms;

linear or branched alkyl radicals comprising 1 to 4 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;

X is chosen from:
linear or branched alkyl radicals comprising 1 to 14 carbon atoms and alkenyl radicals comprising 2 to 14 carbon atoms, wherein said alkyl radicals and said alkenyl radicals are optionally interrupted with at least one entity chosen from hetero atoms and groups comprising at least one hetero atom and are optionally substituted with at least one entity chosen from hetero atoms, groups comprising at least one hetero atom, and halogen atoms;

5- or 6-membered heterocyclic radicals optionally substituted with at least one entity chosen from
linear or branched alkyl radicals comprising 1 to 14 carbon atoms, optionally substituted with at least one hetero atom;
linear or branched aminoalkyl radicals comprising 1 to 4 carbon atoms, optionally substituted with at least one hetero atom; and
halogen atoms;

fused or non-fused aromatic or diaromatic radicals, optionally separated with at least one alkyl radical comprising 1 to 4 carbon atoms, the aromatic or diaromatic radicals optionally being substituted with at least one entity chosen from halogen atoms and alkyl radicals comprising 1 to 10 carbon atoms, wherein said alkyl radicals comprising 1 to 10 carbon atoms are optionally interrupted with at least one entity chosen from hetero atoms and groups comprising at least one hetero atom and are optionally substituted with at least one entity chosen from hetero atoms and groups comprising at least one hetero atom;

dicarbonyl radicals;
the group X optionally comprising at least one cationic charge;

a is chosen from 0 and 1;
$Y^-$, which may be identical or different, is chosen from organic and mineral anions; and
n is an integer at least equal to 2 and at most equal to the number of cationic charges present in the at least one fluorescent dye; and at least one compound comprising an acid functional group, with a molecular weight of less than 500 g/mol, chosen from mineral compounds and organic compounds comprising at least one entity chosen from carboxylic functional groups, sulphonic functional groups, linear or branched, saturated or unsaturated, hydrocarbon-based radicals comprising 1 to 30 carbon atoms, and aromatic radicals comprising 6 to 30 carbon atoms, wherein said hydrocarbon-based radicals are optionally substituted with at least one entity chosen from hetero atoms, groups comprising at least one hetero atom, and halogen atoms, and are optionally interrupted with at least one entity chosen from hetero atoms and groups comprising at least one heteroatom;

drying the skin or leaving the skin to dry.

45. A multi-compartment device for dyeing and lightening keratin fibers, comprising
at least one compartment comprising a dye composition comprising, in a cosmetically acceptable medium,
at least one fluorescent dye that is soluble in said medium chosen from the following formulae:

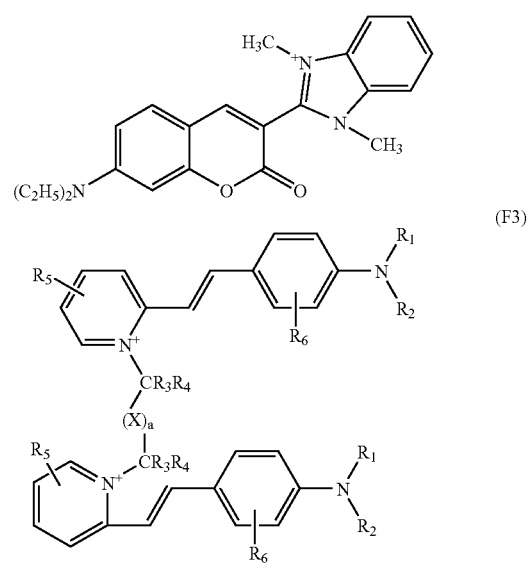

in which:
$R_1$ and $R_2$, which may be identical or different, are chosen from:
hydrogen atoms;
linear or branched alkyl radicals comprising 1 to 10 carbon atoms, optionally interrupted with at least one entity chosen from hetero atoms and
groups comprising at least one hetero atom and optionally substituted with at least one entity chosen from hetero atoms, groups comprising at least one hetero atom, and halogen atoms;
aryl and arylalkyl radicals, the aryl radicals comprising 6 carbon atoms and the alkyl groups comprising 1 to 4 carbon atoms; the aryl groups optionally being substituted with at least one linear or branched alkyl radical comprising 1 to 4 carbon atoms, wherein said at least one alkyl radical is optionally interrupted with at least one entity chosen from hetero atoms and groups comprising at least one hetero atom and is optionally substituted with at least one entity chosen from hetero atoms, groups comprising at least one hetero atom, and halogen atoms;
$R_1$ and $R_2$ may optionally be linked so as to form a heterocycle with the nitrogen atom to which they are attached and may comprise at least one other hetero atom, the heterocycle optionally being substituted with at least one linear or branched alkyl radical, wherein the at least one alkyl radical is optionally interrupted with at least one entity chosen from hetero atoms and groups comprising at least one hetero atom and is optionally substituted with at least one entity chosen from hetero atoms, groups comprising at least one hetero atom, and halogen atoms;
$R_1$ or $R_2$ may optionally form a heterocycle comprising the nitrogen atom to which they are attached and one of the carbon atoms of the phenyl group comprising the nitrogen atom;
$R_3$ and $R_4$, which may be identical or different, are chosen from hydrogen atoms and alkyl radicals comprising 1 to 4 carbon atoms;
$R_5$, which may be identical or different, are chosen from hydrogen atoms, halogen atoms, and linear or branched alkyl radicals comprising 1 to 4 carbon atoms, optionally interrupted with at least one hetero atom;
$R_6$, which may be identical or different, is chosen from hydrogen atoms: halogen atoms;
linear or branched alkyl radicals comprising 1 to 4 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;
X is chosen from:
linear or branched alkyl radicals comprising 1 to 14 carbon atoms and alkenyl radicals comprising 2 to 14 carbon atoms, wherein said alkyl radicals and said alkenyl radicals are optionally interrupted with at least one entity chosen from hetero atoms and groups comprising at least one hetero atom and are optionally substituted with at least one entity chosen from hetero atoms, groups comprising at least one hetero atom, and halogen atoms;
5- or 6-membered heterocyclic radicals optionally substituted with at least one entity chosen from
linear or branched alkyl radicals comprising 1 to 14 carbon atoms, optionally substituted with at least one hetero atom;
linear or branched aminoalkyl radicals comprising 1 to 4 carbon atoms, optionally substituted with at least one hetero atom; and
halogen atoms;
fused or non-fused aromatic or diaromatic radicals, optionally separated with at least one alkyl radical comprising 1 to 4 carbon atoms, the aromatic or diaromatic radicals optionally being substituted with at least one entity chosen from halogen atoms and alkyl radicals comprising 1 to 10 carbon atoms, wherein said alkyl radicals comprising 1 to 10 carbon atoms are optionally interrupted with at least one entity chosen from hetero atoms and groups comprising at least one hetero atom and are optionally substituted with at least one entity chosen from hetero atoms and groups comprising at least one hetero atom;
dicarbonyl radicals;
the group X optionally comprising at least one cationic charge;
a is chosen from 0 and 1;
$Y^-$, which may be identical or different, is chosen from organic and mineral anions; and
n is an integer at least equal to 2 and at most equal to the number of cationic charges present in the at least one fluorescent dye; and
at least one compound comprising an acid functional group, with a molecular weight of less than 500 g/mol, chosen from mineral compounds and organic compounds comprising at least one entity chosen from carboxylic functional groups, sulphonic functional groups, linear or branched, saturated or unsaturated, hydrocarbon-based radicals comprising 1 to 30 carbon atoms, and aromatic radicals comprising 6 to 30 carbon atoms, wherein said hydrocarbon-based radicals are optionally substituted with at least one entity chosen from hetero atoms, groups comprising at least one hetero atom, and halogen atoms, and are optionally interrupted with at least one entity chosen from hetero atoms and groups comprising at least one heteroatom;
at least one other compartment comprising a composition comprising at least one oxidizing agent.

46. A process for dyeing keratin materials with a lightening effect comprising,
applying to keratin materials a dye composition comprising, in a cosmetically acceptable medium, at least one fluorescent dye that is soluble in the medium chosen from the following formulae:

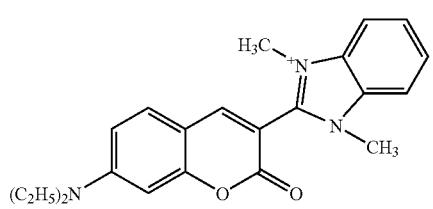

(F1)

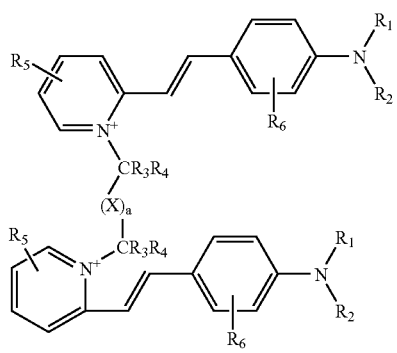

(F3)

in which:
$R_1$ and $R_2$, which may be identical or different, are chosen from:

hydrogen atoms;
linear or branched alkyl radicals comprising 1 to 10 carbon atoms, optionally interrupted with at least one entity chosen from hetero atoms and
groups comprising at least one hetero atom and optionally substituted with at least one entity chosen from hetero atoms, groups comprising at least one hetero atom, and halogen atoms;
aryl and arylalkyl radicals, the aryl radicals comprising 6 carbon atoms and the alkyl groups comprising 1 to 4 carbon atoms; the aryl groups optionally being substituted with at least one linear or branched alkyl radical comprising 1 to 4 carbon atoms, wherein said at least one alkyl radical is optionally interrupted with at least one entity chosen from hetero atoms and groups comprising at least one hetero atom and is optionally substituted with at least one entity chosen from hetero atoms, groups comprising at least one hetero atom, and halogen atoms;
$R_1$ and $R_2$ may optionally be linked so as to form a heterocycle with the nitrogen atom to which they are attached and may comprise at least one other hetero atom, the heterocycle optionally being substituted with at least one linear or branched alkyl radical, wherein the at least one alkyl radical is optionally interrupted with at least one entity chosen from hetero atoms and groups comprising at least one hetero atom and is optionally substituted with at least one entity chosen from hetero atoms, groups comprising at least one hetero atom, and halogen atoms;
$R_1$ or $R_2$ may optionally form a heterocycle comprising the nitrogen atom to which they are attached and one of the carbon atoms of the phenyl group comprising the nitrogen atom;
$R_3$ and $R_4$, which may be identical or different, are chosen from hydrogen atoms and alkyl radicals comprising 1 to 4 carbon atoms;
$R_5$, which may be identical or different, are chosen from hydrogen atoms, halogen atoms, and linear or branched alkyl radicals comprising 1 to 4 carbon atoms, optionally interrupted with at least one hetero atom;
$R_6$, which may be identical or different, is chosen from hydrogen atoms; halogen atoms;
linear or branched alkyl radicals comprising 1 to 4 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;
X is chosen from:
linear or branched alkyl radicals comprising 1 to 14 carbon atoms and alkenyl radicals comprising 2 to 14 carbon atoms, wherein said alkyl radicals and said alkenyl radicals are optionally interrupted with at least one entity chosen from hetero atoms and groups comprising at least one hetero atom and are optionally substituted with at least one entity chosen from hetero atoms, groups comprising at least one hetero atom, and halogen atoms;
5- or 6-membered heterocyclic radicals optionally substituted with at least one entity chosen from
linear or branched alkyl radicals comprising 1 to 14 carbon atoms, optionally substituted with at least one hetero atom;
linear or branched aminoalkyl radicals comprising 1 to 4 carbon atoms, optionally substituted with at least one hetero atom; and
halogen atoms;

fused or non-fused aromatic or diaromatic radicals, optionally separated with at least one alkyl radical comprising 1 to 4 carbon atoms, the aromatic or diaromatic radicals optionally being substituted with at least one entity chosen from halogen atoms and alkyl radicals comprising 1 to 10 carbon atoms, wherein said alkyl radicals comprising 1 to 10 carbon atoms are optionally interrupted with at least one entity chosen from hetero atoms and groups comprising at least one hetero atom and are optionally substituted with at least one entity chosen from hetero atoms and groups comprising at least one hetero atom;
dicarbonyl radicals;
the group X optionally comprising at least one cationic charge;
a is chosen from 0 and 1:
$Y^-$, which may be identical or different, is chosen from organic and mineral anions; and
n is an integer at least equal to 2 and at most equal to the number of cationic charges present in the at least one fluorescent dye of formula (F4):

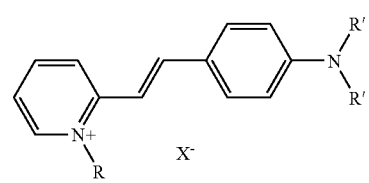

in which formula R is chosen from methyl and ethyl radicals; R' is a methyl radical, and X- is an anion; and
at least one compound comprising an acid functional group, with a molecular weight of less than 500 g/mol, chosen from mineral compounds and organic compounds comprising at least one entity chosen from carboxylic functional groups, sulphonic functional groups, linear or branched, saturated or unsaturated hydrocarbon-based radicals comprising from 1 to 30 carbon atoms, and aromatic radicals comprising from 6 to 30 carbon atoms, wherein said hydrocarbon-based radicals are optionally substituted with at least one entity chosen from hetero atoms, groups comprising at least one hetero atom, and halogen atoms and are optionally interrupted with at least one entity chosen from hetero atoms and groups comprising at least one heteroatom.

47. A process according to claim 46, wherein the at least one fluorescent dye gives a reflectance maximum that is in the wavelength range from 500 to 650 nanometers.

48. A process according to claim 47, wherein the at least one fluorescent dye gives a reflectance maximum that is in the wavelength range from 550 to 620 nanometers.

49. A process according to claim 48, wherein the at least one fluorescent dye is a dye in the orange range.

50. A compound according to claim 46, wherein $R_1$ and $R_2$, which may be identical or different, are chosen from linear or branched alkyl radicals comprising 1 to 4 carbon atoms.

51. A compound according to claim 46, wherein $R_1$ and $R_2$ are linked so as to form a heterocycle comprising the nitrogen atom and comprise at least one hetero atom, wherein the heterocycle is optionally substituted with at least one linear or branched alkyl radical comprising 1 to 4 carbon atoms.

52. A process according to claim 46, wherein in formula (F4) X- is an anion chosen from chloride, iodide, sulphate, methosulphate, acetate, and perchlorate ions.

53. A process according to claim 46, wherein the keratin materials are chosen from artificially colored and/or pigmented keratin fibers and dark skin.

54. A process according to claim 53, wherein the artificially colored and/or pigmented keratin fibers are hair.

55. A process according to claim 54, wherein the hair has a tone height of less than or equal to 6.

56. A process according to claim 55, wherein the hair has a tone height of less than or equal to 4.

* * * * *

UNITED STATES PATENT AND TRADEMARK OFFICE
CERTIFICATE OF CORRECTION

| | | |
|---|---|---|
| PATENT NO. | : 7,186,278 B2 | Page 1 of 1 |
| APPLICATION NO. | : 10/814430 | |
| DATED | : March 6, 2007 | |
| INVENTOR(S) | : Grégory Plos and Luc Gourlaouen | |

It is certified that error appears in the above-identified patent and that said Letters Patent is hereby corrected as shown below:

Column 25, line 35, "heteroato" should read --hetero atom--.

Signed and Sealed this

Fifteenth Day of May, 2007

JON W. DUDAS
*Director of the United States Patent and Trademark Office*